US008880157B2

(12) United States Patent
Buckley

(10) Patent No.: US 8,880,157 B2
(45) Date of Patent: Nov. 4, 2014

(54) METHODS, DEVICES AND A MARKER FOR PHYSICAL CONDITION TESTING

(75) Inventor: Jonathan David Buckley, Aberfoyle Park (AU)

(73) Assignee: University of South Australia, South Australia (AU)

( * ) Notice: Subject to any disclaimer, the term of this patent is extended or adjusted under 35 U.S.C. 154(b) by 0 days.

(21) Appl. No.: 13/807,693

(22) PCT Filed: Jun. 29, 2011

(86) PCT No.: PCT/AU2011/000804
§ 371 (c)(1),
(2), (4) Date: Mar. 15, 2013

(87) PCT Pub. No.: WO2012/000034
PCT Pub. Date: Jan. 5, 2012

(65) Prior Publication Data
US 2013/0172764 A1    Jul. 4, 2013

(30) Foreign Application Priority Data
Jun. 30, 2010   (AU) ............................... 2010902911

(51) Int. Cl.
| | | |
|---|---|---|
| *A61B 5/04* | (2006.01) | |
| *A61B 5/0205* | (2006.01) | |
| *A61B 5/0402* | (2006.01) | |
| *A61B 5/00* | (2006.01) | |
| *A63B 24/00* | (2006.01) | |
| *A61B 5/0245* | (2006.01) | |
| *A61B 5/024* | (2006.01) | |

(52) U.S. Cl.
CPC .............. *A61B 5/0245* (2013.01); *A61B 5/0205* (2013.01); *A61B 5/0402* (2013.01); *A63B 2230/06* (2013.01); *A61B 5/7246* (2013.01); *A63B 24/0075* (2013.01); *A61B 5/04012* (2013.01); *A61B 5/4842* (2013.01); *A61B 5/024* (2013.01)
USPC ......................................................... 600/509

(58) Field of Classification Search
CPC .... A61B 5/0205; A61B 5/024; A61B 5/0245; A61B 5/04012; A61B 5/0402; A61B 5/4842; A61B 5/7246; A63B 2230/06; A63B 24/0075
USPC ......................................................... 600/509
See application file for complete search history.

(56) References Cited

U.S. PATENT DOCUMENTS

| | | | |
|---|---|---|---|
| 7,043,294 B1 | 5/2006 | Paris | |
| 2009/0076347 A1* | 3/2009 | Anderson et al. | ............. 600/301 |
| 2009/0287103 A1* | 11/2009 | Pillai | ............................. 600/509 |

OTHER PUBLICATIONS

Pelletier, R. et al., "The Role of Mood Disorders in Exercise-Induced Cardiovascular Reactivity," *Psychosomatic Medicine* (2009, 71:301-307, 7 pages.

(Continued)

*Primary Examiner* — George Manuel
(74) *Attorney, Agent, or Firm* — Inskeep IP Group, Inc.

(57) ABSTRACT

The present invention relates to methods and devices for testing the physical condition of an individual. The methods and devices rely on the use of a marker of physical condition, and have applications including determining an individuals state of physical recovery from prior physical or athletic activity, determining an individuals physiological readiness for optimal physical performance, determining changes in the risk of (or for assessing progression of) cardiovascular disease in an individual, and for determining exercise and/or athletic training instructions for an individual based on their recovery state, physiological readiness to perform, and/or their cardiovascular disease risk status. The methods and devices require a comparison between the rate of increase in heart rate of an individual during a sub-maximal physical activity, and a predetermined reference measurement. A rate of increase in heart rate which is faster or slower than the predetermined reference measurement will allow determination of the individuals recovery state, physiological readiness to perform, and/or their cardiovascular disease risk status.

20 Claims, 14 Drawing Sheets

(56) References Cited

OTHER PUBLICATIONS

Lamberts, R.P. et al., "Measuring Submaximal Performance Parameters to Monitor Fatigue and Predict Cycling Performance: A Case Study of a World-Class Cyclo-Cross Cyclist," *Eur J Appl Physiol,* Nov. 18, 2009, 108:183-190, 8 pages.

Kiviniemi, A.M. et al., "Endurance Training Guided Individually by Daily Heart Rate Variability Measurements," *Eur J Appl Physiol* (2007), 101: 743-751, 9 pages.

Achten, J. et al., "Heart Rate Monitoring: Applications and Limitations," *Sports Med* 2003, 33(7): 517-538, 23 pages.

Lamberts, R.P. et al., "Day-To-Day Variation in Heart Rate At Different Levels of Submaximal Exertion: Implications for Monitoring Training," *Journal of Strength and Conditioning Research,* May 2009; 23, 3; pp. 1005-1010, 6 pages.

Lamberts, R.P. et al., "Variation in Heart Rate During Submaximal Exercise: Implications for Monitoring Training," *Journal of Strength and Conditioning Research,* 2004, 18(3), 641-645, 6 pages.

\* cited by examiner

FIGURE 2
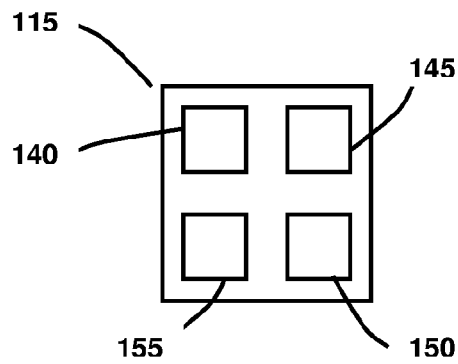
Figure 2a
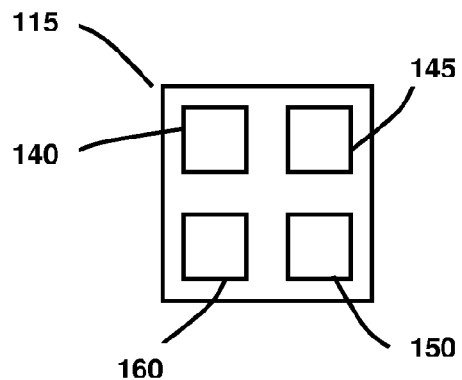
Figure 2b
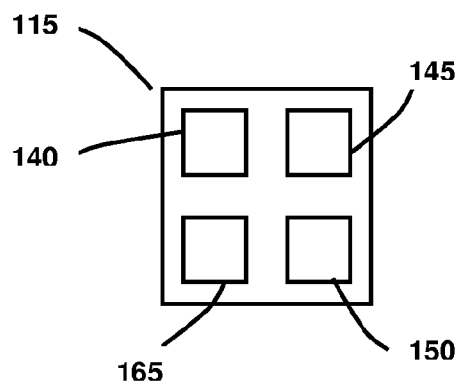
Figure 2c
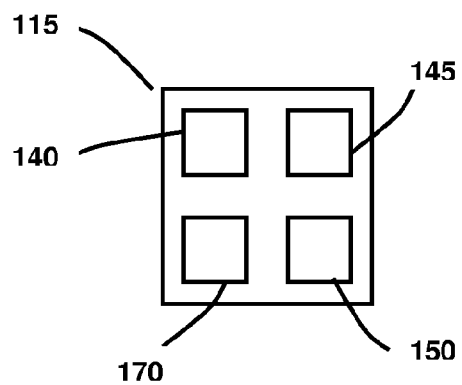
Figure 2d
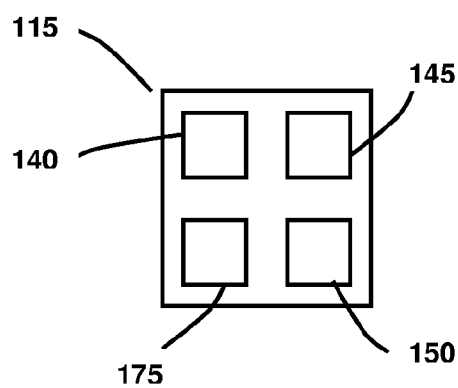
Figure 2e

METHODS, DEVICES AND A MARKER FOR PHYSICAL CONDITION TESTING

RELATED APPLICATIONS

This application is the U.S. National Phase of international patent application number PCT/AU2011/000804, International Filing Date Jun. 29, 2011, entitled Methods, Devices And A Marker For Physical condition Testing, which claims priority to Australian provisional patent application 2010902911 filed on 30 Jun. 2010, entitled Methods And Devices For Determining Physical Recovery And Physical Performance Capacity, both of which are herein incorporated by reference in their entireties.

FIELD OF THE INVENTION

The present invention relates generally to the field of physical condition testing, and to a physiological marker associated with an individual's physical condition. Methods and devices incorporating this marker are also contemplated. Such methods and devices can be used for determining the individual's state of physical recovery from prior physical or athletic activity, for determining the individual's physiological readiness for optimal physical performance, for determining changes in the risk of (or for assessing progression of) cardiovascular disease in the individual, and for determining exercise and/or athletic training instructions for the individual based on their recovery state, physiological readiness to perform, and/or their cardiovascular disease risk status.

BACKGROUND OF THE INVENTION

A number of testing systems are relied upon to determine the physical condition of an individual. These systems include measuring physiological parameters in the individual such as their anaerobic or lactic acid threshold, maximal oxygen uptake ($VO_2$ max), maximal heart rate, heart rate variability (i.e. beat-to-beat alterations in heart rate), heart rate recovery, and muscle sympathetic nerve activity (MSNA).

For example, it is known that exercise training increases heart muscle function so that for each beat, the heart's capability to deliver blood to the tissues, including skeletal muscles, is increased and, when combined with training induced increases in the ability of skeletal muscles to extract and utilise oxygen from the blood, results in an increase in $VO_2$ max. Exercise training also alters the mobilisation and usage of fuel molecules by skeletal muscle such that more fat is oxidised with less reliance on carbohydrate as a fuel, which reduces blood lactic acid concentrations and increases the lactic acid or anaerobic threshold. Therefore, it is generally accepted that the better condition an individual is in, the higher will be their $VO_2$ max and lactate threshold, and the lower their heart rate with the same exercise workload. This lower heart rate at the same exercise workload is attributable to an increased stroke volume, and thus requires reduced activity of the sympathetic division of the autonomic nervous system. Thus, a person in better physical condition will have a lower heart rate at any given exercise workload, reflecting reduced sympathetic nervous system activity.

Furthermore, decrements in physical performance have been associated with changes in beat-to-beat variation in heart rate and heart rate recovery, which reflect alterations in the balance of activity between the sympathetic and parasympathetic divisions of the autonomic nervous system, and MSNA, which reflects the level of activity of sympathetic neurons supplying skeletal muscle.

Alterations in the balance of activity between the sympathetic and parasympathetic divisions of the autonomic nervous system have also been identified in the pathogenesis of a number of cardiovascular diseases, including coronary artery disease, hypertension, congestive heart failure, arrhythmias and sudden cardiac death. The magnitude of the autonomic imbalance correlates with the severity of the disease, and favours an increasing predominance of sympathetic activity and reduced parasympathetic activity. Small changes in autonomic balance that precede the presence of overt disease could therefore be predictive of future cardiovascular disease risk. Accordingly, measures which are able to sensitively detect changes in autonomic balance that precede the presence of overt disease will be useful for predicting future cardiovascular disease risk and/or tracking disease progression.

Measurement of physiological parameters related to autonomic balance presents its problems. For example, the "gold standard" method of measuring variations in beat-to-beat heart rate responses to assess heart rate variability requires an individual to lie quietly for up to twenty minutes while an electrocardiogram is recorded, and then requires specific expertise to analyse the recording.

Measurement of physiological parameters related to exercise performance also presents challenges. $VO_2$ max and anaerobic threshold tests often rely on an individual performing progressive physical exercise over time to a maximum effort, with analysis of gas concentrations in expired air and blood sampling occurring periodically during the exercise to measure for oxygen uptake and the levels of lactic acid in the individual's blood. Other tests such as the Astrand-Rhyming test involve the individual exercising at a sub-maximal capacity for a period of time to achieve a steady-state heart rate and then using a nomogram to predict their maximal oxygen uptake from the relationship between heart rate and exercise workload, or the Conconi test in which an individual's running speed is plotted against their heart rate for predetermined distance intervals, again both require maximal exercise. Still further, tests which determine MSNA require measurements of nerve activity in the peroneal nerve using the microneurography technique which includes the use of invasive procedures and sophisticated machinery not typically available to all.

Accordingly, the aforementioned tests are either overly invasive, expensive or require specific high-level expertise to conduct (and are therefore impractical for a majority of individuals), are inaccurate, or they only provide meaningful results if the individual being tested can perform an aerobic activity to their maximal capacity, which is not always possible or recommended, particularly in individuals who may have some underlying medical condition.

Furthermore, it is often necessary to measure multiple parameters to achieve a complete overall idea of the physiological status of an individual, as single measures, such as $VO_2$ max, when taken alone, are not always useful for predicting athletic performance. For example, two individuals may have the same $VO_2$ max but one may consistently perform better than the other in athletic competition because the lactic acid threshold of the former individual may be higher than that of the latter. Thus, there is at present no single testing method which can provide a complete indication of the physiological readiness to perform an athletic activity, and thereby predict athletic performance, other than to have an individual undertake the performance, which is not always possible or practical.

Athletic training to improve sporting performance is based on the principle that progressively overloading physiological systems, with adequate recovery time for adaptation to take place, results in improved performance. However, if insufficient recovery occurs after a bout of exercise before an additional load is undertaken, then this can lead to over-reaching, with a temporary reduction in performance. If additional overload is then maintained this may lead to a state of over-training with long-term performance deficits and adverse impacts on the health of the individual.

There are a number of physiological, biochemical, psychological and immunological signs and symptoms that have been associated with over-reaching or over-training. However, tests that can identify markers which precede the ultimate drop in performance associated with these signs and symptoms have not been available. Unfortunately, due to the inherent limitations of the tests described above, they do not allow the physical status of an individual to be determined in terms of their readiness to perform exercise in an accurate, meaningful, and/or practical manner.

Similarly, there is currently no objective method or test for determining the recovery state of an individual, such as an athlete, and/or to predict the athlete's ability to perform an athletic activity after a period of recovery that is widely accepted other than to get them to undergo a performance test and compare the level of performance achieved with a measure that was taken when the athlete was known to be fully recovered. This approach has the disadvantage in that it can interfere with the training program of the athlete and, if the athlete is becoming over-trained, additional maximal exercise performance testing would only serve to worsen their condition. Furthermore, if the individual is very unfit, or has a serious medical condition such as cardiovascular disease, they simply may not have the capacity to undergo a maximal exercise performance test, and in some cases performance of such a test could prove life threatening for the individual.

Therefore, methods and devices for assessing the recovery state of an individual and/or predicting the individual's ability to perform an athletic activity at their optimal capacity are required. Such tests would be invaluable to an individual or athlete, including their coach and/or sport physiologist, for fitness or training purposes (including the design of appropriate training programs), and for achieving ultimate physical performance in their particular athletic pursuit. If such tests are also able to sensitively detect changes in autonomic balance that precede the presence of disease, then they will also be useful for predicting the future risk of cardiovascular disease and/or for monitoring disease progression in the wider (non-athletic) population.

Reference herein to a patent document or other matter which is given as prior art in this specification is not, and should not be taken as, an acknowledgment or any form of suggestion that this prior art forms part of the common general knowledge in any country as at the priority date of any of the claims in this application.

SUMMARY OF THE INVENTION

The present invention arises out of studies investigating whether changes in heart rate during sub-maximal exercise, of a similar intensity to that which would be undertaken by an individual during a warm-up preceding exercise, athletic training or athletic competition, could provide an insight into what might be a useful marker of (1) the recovery state of the individual, (2) the physiological readiness of the individual to perform an athletic activity to, above, or below, their optimal capacity, (3) the individual's future risk of developing cardiovascular disease, and/or (4) the progression of cardiovascular disease in the individual.

These physical condition testing studies established that the rate of increase in heart rate during sub-maximal exercise at either a self-selected or fixed workload was positively related to exercise performance of the individual during a maximal exercise performance test performed immediately after the sub-maximal exercise. The maximal performance test being one related to cardiorespiratory fitness.

These studies also established that the rate of increase in heart rate during sub-maximal exercise at either a fixed or self-selected workload was decreased following fatiguing exercise and that this was associated with reduced exercise performance.

These studies also established that the rate of increase in heart rate during sub-maximal exercise was related to two recognised risk factors for cardiovascular disease, one being age and the other being cardiorespiratory fitness (as indicated by performance during a 5 minute maximal exercise performance test), with the rate of heart rate increase during sub-maximal exercise being inversely correlated with age (in years) and positively correlated with maximal exercise performance (i.e. a marker of cardiorespiratory fitness).

Accordingly, in a first aspect, the present invention provides a method for determining a recovery state of an individual from an athletic activity, the method including:
(a) subjecting the individual to a sub-maximal physical activity;
(b) measuring the heart rate of the individual during the sub-maximal physical activity;
(c) determining the rate of increase in heart rate of the individual during the sub-maximal physical activity;
(d) comparing the determined rate of increase in heart rate of the individual with a predetermined reference measurement; and
(e) determining the recovery state of the individual from the athletic activity on the basis of the comparison.

As used in the specification, the term "rate of increase in heart rate" refers to the speed with which the heart rate of an individual increases in a specified time recordal period during the sub-maximal physical activity. For example, if the specified time period for recording the heart rate of an individual is five minutes, the rate of increase in heart rate of the individual will be a measure of how quickly the heart rate of the person has increased from its resting level during that five minute period.

In a second aspect, the present invention provides a method for predicting an individual's ability to perform an athletic activity at, above, or below, their optimal capacity, the method including:
(a) subjecting the individual to a sub-maximal physical activity prior to the athletic activity;
(b) measuring the heart rate of the individual during the sub-maximal physical activity;
(c) determining the rate of increase in heart rate of the individual during the sub-maximal physical activity;
(d) comparing the determined rate of increase in heart rate of the individual with a predetermined reference measurement; and
(e) predicting the individual's ability to perform the athletic activity at, above, or below, their optimal capacity on the basis of the comparison.

As described above and discussed further herein, the inventor has established that the rate of increase in heart rate during sub-maximal exercise is related to two recognised risk factors for cardiovascular disease, namely age and cardiorespiratory fitness.

Accordingly, in a third aspect, the present invention provides a method for determining a change in the risk of cardiovascular disease developing in an individual, the method including:
  (a) subjecting the individual to a sub-maximal physical activity;
  (b) measuring the heart rate of the individual during the sub-maximal physical activity;
  (c) determining the rate of increase in heart rate of the individual during the sub-maximal physical activity;
  (d) comparing the determined rate of increase in heart rate of the individual with a predetermined reference measurement; and
  (e) determining a change in the risk of cardiovascular disease developing in the individual on the basis of the comparison.

In a fourth aspect, the present invention provides a method for assessing the progression of cardiovascular disease in an individual, the method including:
  (a) subjecting the individual to a sub-maximal physical activity;
  (b) measuring the heart rate of the individual during the sub-maximal physical activity;
  (c) determining the rate of increase in heart rate of the individual during the sub-maximal physical activity;
  (d) comparing the determined rate of increase in heart rate of the individual with a predetermined reference measurement; and
  (e) assessing the progression of cardiovascular disease in the individual on the basis of the comparison.

In some embodiments of the aforementioned aspects of the invention, a heart rate monitor is used to measure the heart rate of the individual during the sub-maximal physical activity. The heart rate monitor may also determine the rate of increase in heart rate of the individual during the sub-maximal physical activity.

Given that the inventor has determined that the rate of increase in heart rate during a sub-maximal physical activity is positively related to subsequent exercise performance, and is related to two recognised risk factors for cardiovascular disease, this marker can be incorporated into a device for physical condition testing.

Accordingly, in a fifth aspect, the present invention provides a device for determining a recovery state of an individual from an athletic activity, the device including:
  (a) a heart rate measurement unit for measuring the heart rate of the individual during a sub-maximal physical activity;
  (b) a rate of increase in heart rate determination unit for determining the rate of increase in heart rate of the individual during the sub-maximal physical activity;
  (c) a comparison unit for performing a comparison between the determined rate of increase in heart rate of the individual and a predetermined reference measurement; and
  (d) a recovery state determination unit for determining the recovery state of the individual from the athletic activity on the basis of the comparison.

In a sixth aspect, the present invention provides a device for predicting an individual's ability to perform an athletic activity at, above, or below, their optimal capacity, the device including:
  (a) a heart rate measurement unit for measuring the heart rate of the individual during a sub-maximal physical activity;
  (b) a rate of increase in heart rate determination unit for determining the rate of increase in heart rate of the individual during the sub-maximal physical activity;
  (c) a comparison unit for performing a comparison between the determined rate of increase in heart rate of the individual and a predetermined reference measurement; and
  (d) a prediction determination unit for predicting the individual's ability to perform the athletic activity at, above, or below, their optimal capacity on the basis of the comparison.

In a seventh aspect, the present invention provides a device for determining a change in the risk of cardiovascular disease developing in an individual, the device including:
  (a) a heart rate measurement unit for measuring the heart rate of the individual during a sub-maximal physical activity;
  (b) a rate of increase in heart rate determination unit for determining the rate of increase in heart rate of the individual during the sub-maximal physical activity;
  (c) a comparison unit for performing a comparison between the determined rate of increase in heart rate of the individual and a predetermined reference measurement; and
  (d) a cardiovascular disease risk determination unit for determining a change in the risk of cardiovascular disease developing in the individual on the basis of the comparison.

In an eighth aspect, the present invention provides a device for assessing the progression of cardiovascular disease in an individual, the device including:
  (a) a heart rate measurement unit for measuring the heart rate of the individual during a sub-maximal physical activity;
  (b) a rate of increase in heart rate determination unit for determining the rate of increase in heart rate of the individual during the sub-maximal physical activity;
  (c) a comparison unit for performing a comparison between the determined rate of increase in heart rate of the individual and a predetermined reference measurement; and
  (d) a cardiovascular disease progression assessment unit for assessing the progression of cardiovascular disease in the individual on the basis of the comparison.

In some embodiments of the fifth to eighth aspects of the invention, the device further includes a display unit for displaying the recovery state of the individual from the athletic activity, for displaying the individual's predicted ability to perform the athletic activity at, above, or below, their optimal capacity, for determining a change in the risk of cardiovascular disease developing in the individual, and/or for assessing the progression of cardiovascular disease in the individual.

In some embodiments of the aforementioned aspects of the invention, the slower the rate of increase in heart rate of the individual during the sub-maximal physical activity compared to the predetermined reference measurement, the lower the recovery state of the individual from the athletic activity and/or the higher the likelihood the individual will perform the athletic activity below their optimal capacity.

In some embodiments of the aforementioned aspects of the invention, a slower rate of increase in heart rate of the individual during the sub-maximal physical activity compared to the predetermined reference measurement indicates that the risk of cardiovascular disease developing in the individual has increased, and/or is indicative of the progression of cardiovascular disease in the individual.

In some embodiments of the aforementioned aspects of the invention, if the rate of increase in heart rate of the individual during the sub-maximal physical activity is the same as the predetermined reference measurement, the individual has recovered from the athletic activity, and/or the higher the likelihood the individual will perform the athletic activity at their optimal capacity.

In some embodiments of the aforementioned aspects of the invention, if the rate of increase in heart rate of the individual during the sub-maximal physical activity is faster than the predetermined reference measurement, the individual has recovered from the athletic activity and has improved fitness, and/or the higher the likelihood the individual will perform the athletic activity above their optimal capacity.

In some embodiments of the aforementioned aspects of the invention, a faster rate of increase in heart rate of the individual during the sub-maximal physical activity compared to the predetermined reference measurement indicates that the risk of cardiovascular disease developing in the individual has decreased, and/or is indicative of an improvement of cardiovascular disease in the individual.

In some embodiments of the aforementioned aspects of the invention, the heart rate of the individual may be measured during the 30 seconds preceding sub-maximal physical activity and during the first five minutes of the sub-maximal physical activity.

In some embodiments of the aforementioned aspects of the invention, the sub-maximal physical activity is an activity or a discrete period of exercise that is similar or is the same in exercise intensity to that which would normally be completed during a warm-up preceding athletic training or competition. In some embodiments, the sub-maximal activity is a warm-up activity. In some embodiments, the sub-maximal physical activity can be of either a non-prescribed (i.e. self-selected) or prescribed (i.e. fixed) workload.

In some embodiments of the aforementioned aspects of the invention, the method or device is used to determine exercise instructions for the individual.

In some embodiments of the fifth to eighth aspects of the invention, the device is a heart rate monitor.

In a ninth aspect, the present invention provides a method of determining exercise instructions for an athletic activity for an individual, the method including:
(a) subjecting the individual to a sub-maximal physical activity prior to the athletic activity;
(b) measuring the heart rate of the individual during the sub-maximal physical activity;
(c) determining the rate of increase in heart rate of the individual during the sub-maximal physical activity;
(d) performing a comparison between the determined rate of increase in heart rate of the individual and a predetermined reference measurement; and
(e) determining exercise instructions for the athletic activity on the basis of the comparison.

In an embodiment of the ninth aspect of the invention, if the comparison indicates that the rate of increase in heart rate of the individual during the sub-maximal physical activity is slower than the predetermined reference measurement, the exercise instructions are determined on the basis that the individual is likely to perform the athletic activity below their optimal capacity.

In an alternative embodiment, if the comparison indicates that the rate of increase in heart rate of the individual during the sub-maximal physical activity is faster than the predetermined reference measurement, the exercise instructions are determined on the basis that the individual is capable of performing the athletic activity above their optimal capacity.

In a further alternative embodiment, if the comparison indicates that the rate of increase in heart rate of the individual during the sub-maximal physical activity is the same as the predetermined reference measurement, the exercise instructions are determined on the basis that the individual is capable of performing the athletic activity at their optimal capacity.

In a tenth aspect, the present invention provides a device for determining exercise instructions for an athletic activity for an individual, the device including:
(a) a heart rate measurement unit for measuring the heart rate of the individual during a sub-maximal physical activity conducted prior to the athletic activity;
(b) a rate of increase in heart rate determination unit for determining the rate of increase in heart rate of the individual during the sub-maximal physical activity;
(c) a comparison unit for performing a comparison between the determined rate of increase in heart rate of the individual and a predetermined reference measurement; and
(d) an exercise instruction determination unit for determining exercise instructions for the athletic activity on the basis of the comparison.

In an embodiment of the tenth aspect of the invention, the device further includes a display unit for displaying the exercise instructions for the athletic activity.

In some embodiments of the tenth aspect of the invention, if the comparison unit determines that the rate of increase in heart rate of the individual during the sub-maximal physical activity is slower than the predetermined reference measurement, the exercise instruction determination unit will determine exercise instructions for the athletic activity on the basis that the individual is likely to perform the athletic activity below their optimal capacity.

In some embodiments of the tenth aspect of the invention, if the comparison unit determines that the rate of increase in heart rate of the individual during the sub-maximal physical activity is faster than the predetermined reference measurement, the exercise instruction determination unit will determine exercise instructions for the athletic activity on the basis that the individual is capable of performing the athletic activity above their optimal capacity.

In some embodiments of the tenth aspect of the invention, if the comparison unit determines that the rate of increase in heart rate of the individual during the sub-maximal physical activity is the same as the predetermined reference measurement, the exercise instruction determination unit will determine exercise instructions for the athletic activity on the basis that the individual is capable of performing the athletic activity at their optimal capacity.

In some embodiments of each of the aforementioned aspects of the invention, the method or device is non-invasive. By "non-invasive" is meant that there is no requirement to obtain heart rate measurements by puncturing or breaking the skin of the individual. Furthermore, there is no requirement to perform any type of surgical method or step on the individual, and there is no requirement to make contact with the mucosa or internal body cavities beyond a natural body orifice of the individual.

The marker identified by the inventor can form the basis of a digital media product for determining the physical condition of an individual.

Accordingly, in an eleventh aspect, the present invention provides a computer software product, including coded instructions for executing a computer process in a digital processor, wherein the computer process determines a recovery state of an individual from an athletic activity, and wherein the computer process includes:
(a) inputting a heart rate measurement obtained from the individual during a sub-maximal physical activity conducted prior to the athletic activity;
(b) determining the rate of increase in heart rate of the individual during the sub-maximal physical activity;
(c) performing a comparison between the determined rate of increase in heart rate of the individual and a predetermined reference measurement; and
(d) determining the recovery state of the individual from the athletic activity on the basis of the comparison.

In a twelfth aspect, the present invention provides a computer software product, including coded instructions for executing a computer process in a digital processor, wherein the computer process predicts an individual's ability to perform an athletic activity at, above, or below, their optimal capacity, and wherein the computer process includes:
(a) inputting a heart rate measurement obtained from the individual during a sub-maximal physical activity conducted prior to the athletic activity;
(b) determining the rate of increase in heart rate of the individual during the sub-maximal physical activity;
(c) performing a comparison between the determined rate of increase in heart rate of the individual and a predetermined reference measurement; and
(d) predicting the individual's ability to perform the athletic activity at, above, or below, their optimal capacity on the basis of the comparison.

In thirteenth aspect, the present invention provides a computer software product, including coded instructions for executing a computer process in a digital processor, wherein the computer process determines a change in the risk of cardiovascular disease developing in an individual, and wherein the computer process includes:
(a) inputting a heart rate measurement obtained from the individual during a sub-maximal physical activity;
(b) determining the rate of increase in heart rate of the individual during the sub-maximal physical activity;
(c) performing a comparison between the determined rate of increase in heart rate of the individual and a predetermined reference measurement; and
(d) determining a change in the risk of cardiovascular disease developing in the individual on the basis of the comparison.

In a fourteenth aspect, the present invention provides a computer software product, including coded instructions for executing a computer process in a digital processor, wherein the computer process assesses the progression of cardiovascular disease in an individual, and wherein the computer process includes:
(a) inputting a heart rate measurement obtained from the individual during a sub-maximal physical activity;
(b) determining the rate of increase in heart rate of the individual during the sub-maximal physical activity;
(c) performing a comparison between the determined rate of increase in heart rate of the individual and a predetermined reference measurement; and
(d) assessing the progression of cardiovascular disease in the individual on the basis of the comparison.

In fifteenth aspect, the present invention provides a computer software product, including coded instructions for executing a computer process in a digital processor, wherein the computer process determines exercise instructions for an athletic activity for an individual, and wherein the computer process includes:
(a) inputting a heart rate measurement obtained from the individual during a sub-maximal physical activity conducted prior to the athletic activity;
(b) determining the rate of increase in heart rate of the individual during the sub-maximal physical activity;
(c) performing a comparison between the determined rate of increase in heart rate of the individual and a predetermined reference measurement; and
(d) determining exercise instructions for the athletic activity on the basis of the comparison.

In a further aspect, the present invention provides a computer software distribution means including the computer software product according to any one or more of the eleventh to fifteenth aspects of the invention.

As described herein, the inventor has identified a heart rate parameter which is linked to the physical condition of an individual. Accordingly, in a sixteenth aspect, the present invention provides a marker of a recovery state of an individual from an athletic activity, wherein the marker is the rate of increase in heart rate of the individual during a sub-maximal physical activity.

In a seventeenth aspect, the present invention provides a marker for predicting an individual's ability to perform an athletic activity at, above, or below, their optimal capacity, wherein the marker is the rate of increase in heart rate of the individual during a sub-maximal physical activity.

In an eighteenth aspect, the present invention provides a marker for determining a change in the risk of cardiovascular disease developing in an individual, wherein the marker is the rate of increase in heart rate of the individual during a sub-maximal physical activity.

In a nineteenth aspect, the present invention provides a marker for assessing the progression of cardiovascular disease in an individual, wherein the marker is the rate of increase in heart rate of the individual during a sub-maximal physical activity.

In some embodiments of the sixteenth to nineteenth aspects of the invention, the slower the rate of increase in heart rate of the individual during the sub-maximal physical activity compared to a predetermined reference measurement, the lower the recovery state of the individual from the athletic activity and/or the higher the likelihood the individual will perform the athletic activity below their optimal capacity.

In some embodiments of the aforementioned aspects of the invention, a slower rate of increase in heart rate of the individual during the sub-maximal physical activity compared to a predetermined reference measurement indicates that the risk of cardiovascular disease developing in the individual has increased, and/or is indicative of the progression of cardiovascular disease in the individual.

In some embodiments of the sixteenth to nineteenth aspects of the invention, if the rate of increase in heart rate of the individual during the sub-maximal physical activity is the same as a predetermined reference measurement, the individual has recovered from the athletic activity, and/or the higher the likelihood the individual will perform the athletic activity at their optimal capacity.

In some embodiments of the sixteenth to nineteenth aspects of the invention, if the rate of increase in heart rate of the individual during the sub-maximal physical activity is faster than a predetermined reference measurement, the individual has recovered from the athletic activity and has improved fitness, and/or the higher the likelihood the individual will perform the athletic activity above their optimal capacity.

In some embodiments of the sixteenth to nineteenth aspects of the invention, a faster rate of increase in heart rate of the individual during the sub-maximal physical activity compared to a predetermined reference measurement indicates that the risk of cardiovascular disease developing in the individual has decreased, and/or is indicative of an improvement of cardiovascular disease in the individual.

In some embodiments of the sixteenth to nineteenth aspects of the invention, the heart rate of the individual may be measured during the 30 seconds preceding sub-maximal physical activity and during the first five minutes of the sub-maximal physical activity.

In some embodiments of the sixteenth to nineteenth aspects of the invention, the sub-maximal physical activity is an activity or a discrete period of exercise that is similar in exercise intensity to that which would normally be completed during a warm-up preceding athletic training or competition. The sub-maximal physical activity can be of either a non-prescribed (i.e. self-selected) or prescribed (i.e. fixed) workload.

In some embodiments of the sixteenth to nineteenth aspects of the invention, the method or device is used to determine exercise instructions for the individual.

In some embodiments of the sixteenth to nineteenth aspects of the invention, a heart rate monitor is used to obtain heart rate measurements of the individual during the sub-maximal physical activity.

In some embodiments, the heart rate monitor can determine the rate of increase in heart rate of the individual during the sub-maximal activity.

BRIEF DESCRIPTION OF THE FIGURES

FIG. 2 is a series of detailed schematic drawings of the components included in a processor according to various embodiments of the present invention. FIG. 2a shows a processor for determining a recovery state of an individual from an athletic activity, FIG. 2b shows a processor for predicting an individual's ability to perform an athletic activity at, above, or below, their optimal capacity, FIG. 2c shows a processor for determining a change in the risk of cardiovascular disease developing in an individual, FIG. 2d shows a processor for assessing the progression of cardiovascular disease in an individual, and FIG. 2e shows a processor for determining exercise instructions for an athletic activity for an individual.

DESCRIPTION OF THE INVENTION

Figure 1:
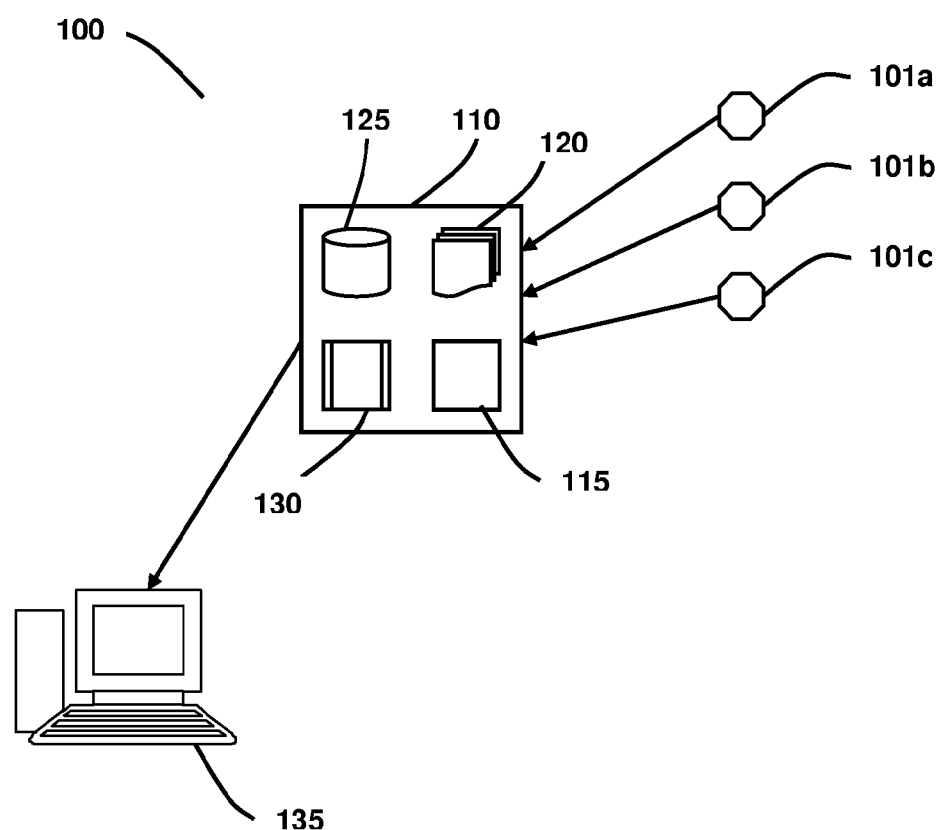
FIG. 1 is a schematic diagram of a device according to an embodiment of the present invention.

It is to be understood that the following description is for the purpose of describing particular embodiments only and is not intended to be limiting with respect to the above description.

The present invention is predicated, in part, on the finding that the rate of increase in heart rate of an individual during sub-maximal exercise (e.g. a warm-up) is positively related to exercise performance of the individual during a maximal exercise performance test conducted immediately after the warm-up. This finding enables the provision of means by which the recovery state of the individual can be determined prior to performance of a subsequent athletic activity.

Accordingly, the present invention provides a method for determining a recovery state of an individual from an athletic activity, the method including:
  (a) subjecting the individual to a sub-maximal physical activity;
  (b) measuring the heart rate of the individual during the sub-maximal physical activity;
  (c) determining the rate of increase in heart rate of the individual during the sub-maximal physical activity;
  (d) comparing the determined rate of increase in heart rate of the individual with a predetermined reference measurement; and (e) determining the recovery state of the individual from the athletic activity on the basis of the comparison.

The inventor's findings also enable the provision of means for determining the likelihood that the individual will be able to perform the athletic activity at, above, or below, their optimal capacity. Accordingly, the present invention also provides a method for predicting an individual's ability to perform an athletic activity at, above, or below, their optimal capacity, the method including:
- (a) subjecting the individual to a sub-maximal physical activity prior to the athletic activity;
- (b) measuring the heart rate of the individual during the sub-maximal physical activity;
- (c) determining the rate of increase in heart rate of the individual during the sub-maximal physical activity;
- (d) comparing the determined rate of increase in heart rate of the individual with a predetermined reference measurement; and
- (e) predicting the individual's ability to perform the athletic activity at, above, or below, their optimal capacity on the basis of the comparison.

An "athletic activity" as used in the specification refers to a physical exercise which is conducted by the individual aimed at achieving an optimal physical performance, or aimed at maintaining or affecting the individual's physical performance. An "athletic activity" will generally encompass an activity with an aerobic exercise component that relies to a large extent on cardiovascular fitness (e.g. an aerobic activity).

The level of physical exertion during the athletic activity will generally vary for each individual. For example, the "athletic activity" of an elite rower, cyclist or runner will involve a high level of physical exertion, where they are often performing the athletic activity at or near their optimal capacity each time. In this instance, the athletic activity may, but need not, relate to the type of physical exercise that the individual performs as part of the athletic pursuit that they are training for. In contrast, the level of exertion of an individual who is simply aiming to keep fit may generally be lower than that of an elite athlete, and need not rely on the individual performing at their optimal capacity each time. Finally, the level of exertion of an individual who has underlying health issues, including cardiovascular disease, or a respiratory disease, disorder or affliction, will generally be quite low and may therefore encompass the performance of day to day activities of daily living.

A "sub-maximal physical activity" as used herein refers to a physical exercise which is less than that requiring a maximal level of exertion. The sub-maximal physical activity would typically be, but is not limited to, an intensity that would be performed during a warm-up activity such as a light jog, or is an activity performed on a cycling, rowing or treadmill or other exercise device at a similar intensity to that which an individual would undertake when warming up prior to performing an athletic activity, as referred to above.

The type of sub-maximal physical activity that the individual is subjected to is not limited to any particular type of activity, or duration of the activity, but should reflect the nature of the subsequent activity for which optimal physical performance is being determined. Therefore, the sub-maximal physical activity can either be of a defined workload (i.e. "prescribed"), or can be chosen by the individual such that it need not be of a defined workload. However, the sub-maximal physical activity must be performed at a steady state (i.e. the individual cannot speed up or slow down) during the recordal period.

As described above, particular aspects of the present invention determine the recovery state of the individual from an athletic activity they have performed. The "recovery state" refers to the extent to which the individual is able to subsequently perform that athletic activity again at their optimal capacity. For example, if a person was to run 1000 meters in three minutes and then repeated the run without having had sufficient time to fully recover but only ran 500 meters in three minutes, then the person would be deemed to have only recovered by fifty percent (i.e. the 500 meter performance was only half of the initial performance of 1000 meters in three minutes).

"Optimal capacity" as used in the specification refers to the individual's previously determined personal best achievable performance for that athletic activity.

Therefore, an individual who has nearly fully recovered, or has indeed reached a full recovery, should be able to perform the athletic activity again near their optimal capacity, or at or above their optimal capacity, respectively. In contrast, an individual who has a low recovery state, i.e. and individual who has partially (that is, not fully) recovered, will not be expected to have the capacity to do so at that time.

As referred to above and described in further below, the present invention provides methods and devices to predict an individual's ability to perform the athletic activity at, above, or below, their optimal capacity. In this regard, an individual that has not fully recovered from an athletic activity will have a reduced likelihood of being able to perform the athletic activity at or above their optimal capacity.

The present invention is also predicated in part on the finding that the rate of increase in heart rate during sub-maximal exercise is related to two recognised risk factors for cardiovascular disease, one being age and the other being cardiorespiratory fitness.

Accordingly, the present invention provides a method for determining a change in the risk of cardiovascular disease developing in an individual, the method including:
- (a) subjecting the individual to a sub-maximal physical activity;
- (b) measuring the heart rate of the individual during the sub-maximal physical activity;
- (c) determining the rate of increase in heart rate of the individual during the sub-maximal physical activity;
- (d) comparing the determined rate of increase in heart rate of the individual with a predetermined reference measurement; and
- (e) determining a change in the risk of cardiovascular disease developing in the individual on the basis of the comparison.

Furthermore, the present invention provides a method for assessing the progression of cardiovascular disease in an individual, the method including:
- (a) subjecting the individual to a sub-maximal physical activity;
- (b) measuring the heart rate of the individual during the sub-maximal physical activity;
- (c) determining the rate of increase in heart rate of the individual during the sub-maximal physical activity;
- (d) comparing the determined rate of increase in heart rate of the individual with a predetermined reference measurement; and
- (e) assessing the progression of cardiovascular disease in the individual on the basis of the comparison.

As would be understood by a person skilled in the art, cardiovascular disease refers to a group of diseases and/or disorders that involve the heart and blood vessels. Examples of a cardiovascular disease or disorder relevant to the present invention include, but are not limited to, coronary artery disease, hypertension, congestive heart failure, arrhythmias and sudden cardiac death. However, it would be understood that any disease or disorder involving heart function is encompassed by the methods and devices of the present invention.

The term "rate of increase in heart rate" does not refer to the actual heart rate of the individual during the time recordal period, nor to the actual amount the heart rate increases by, nor does it refer to the variability in the time interval between individual heart beats (i.e. heart rate variability) during the recordal period, each of which are separate distinct parameters. The rate of increase in heart rate refers to the speed with which the heart rate of an individual increases in a specified time recordal period during the sub-maximal physical activity.

The specified time recordal period may be for less than a minute, or may be as long as five minutes or more. For example the heart rate of the individual may be measured during the first 30 seconds, 60 seconds, 2 minutes, 3 minutes, 4 minutes or 5 minutes of the sub-maximal physical activity, or any amount of time between these values. In a further example, the heart rate of the individual may be measured during the 30 seconds preceding the sub-maximal physical activity and during the first five minutes of the sub-maximal physical activity. As would be known by a person skilled in the art, the rate of increase in heart rate may be derived from multiple recordings of heart rate during the sub-maximal physical activity for the specified time recordal period.

The rate of increase in heart rate per unit time may be determined a number of ways, using methods known to a person skilled in the art. For example, it may be represented by the maximal rate of increase in heart rate, or may be represented by the average rate of increase in heart rate during the time recordal period. For example, the maximal (or average) rate of increase in heart rate may be defined by identifying the maximal (or average) value of the first derivative of an equation describing the relationship between heart rate and time during the specified time recordal period. Alternatively, the rate of increase in heart rate could be determined from the slope of an equation describing the relationship between heart rate and time during the time recordal period.

Generally, the measurement of heart rate per se, or changes in beat-to-beat variation in heart rate (i.e. heart rate variability), during physical exercise provides a reflection of the overall cardiovascular "fitness" of an individual. One aspect of cardiovascular fitness is $VO_2$ max, which is a measure of the amount of oxygen that the body can use per minute in order to provide energy, including energy to perform exercise. It has been previously proposed that the rate of increase in heart rate during light exercise at a prescribed work load might be used to predict the equilibrium, or steady-state, heart rate for that work load. The equilibrium (steady-state) work load might then be used to predict the $VO_2$ max based on a linear relationship between steady-state heart rate and oxygen uptake, in order to provide an assessment of cardiorespiratory "fitness" of an individual and their potential exercise capacity.

In contrast, according to the present invention, measurements of the rate of increase in heart rate of an individual during sub-maximal exercise, such as during their warm-up, provide a reflection of the individual's ability to perform a subsequent athletic activity at their optimal capacity, irrespective of the steady-state (i.e. equilibrium) heart rate achieved during the sub-maximal exercise. This is because the present invention does not rely on a relationship between the rate of heart rate increase and the steady-state heart rate achieved during that exercise, nor does it rely on the steady-state heart rate achieved being used to predict athletic performance. Therefore, two individuals who have similar cardiovascular fitness may have similar steady-state heart rates during the warm-up exercise, but the one who has a faster rate of increase in heart rate (during the time recordal period) will perform better (in terms of their actual exercise performance and/or achieving or exceeding their own optimal capacity) than the other individual.

Accordingly, the present invention may also be used for talent identification, namely to identify or predict which individuals have the potential to be the better performers on the basis of their faster rate of increase in heart rate compared to the other individuals.

In various embodiments of the present invention, the rate of increase in heart rate of the individual, as determined during the sub-maximal physical activity, is compared to a predetermined reference measurement. The "predetermined reference measurement" can be obtained a number of ways depending on the purpose for which the comparison is being made. The predetermined reference measurement may be one which is specific for an individual, or alternatively, the predetermined reference measurement may represent normative data obtained from a number of individuals which have been "matched" (to the subject individual being tested) for a number of parameters, including but not limited to, age, sex, weight, ethnicity, body mass index, smoking status, and health status.

For example, when determining a recovery state of an individual from an athletic activity, or when predicting an individual's ability to perform an athletic activity at, above, or below, their optimal capacity, a predetermined reference measurement will reflect the rate of increase in heart rate of the individual during a sub-maximal physical activity, wherein the individual subsequently performed the relevant athletic activity at their optimal capacity. In this instance, in order to obtain a predetermined reference measurement which is specific for the individual, the optimal capacity of the individual should be assessed when the individual is well rested and unlikely to be suffering from fatigue. A predetermined reference measurement which is specific for an individual may be updated periodically to account for an improvement in the individual's overall fitness as a result of training adaptations. However, as indicated above if a predetermined reference measurement specific for that individual has not previously been obtained for a comparison to be made, the present invention provides for a predetermined reference measurement which is reflective of normative data obtained from a collection of individuals matched for various parameters such as age, sex, weight, ethnicity, body mass index, smoking status, and health status.

When determining a change in the risk of cardiovascular disease developing in an individual, or assessing the progression of cardiovascular disease in an individual, a predetermined reference measurement specific for the individual will serve as a baseline for the cardiovascular health status of the individual at that time. That predetermined reference measurement can for example be taken at the time of a routine health check-up with the individual's general practitioner, or can even be taken by the individual themselves when setting a baseline measurement for future health checks. A change in the risk of, or progression of, cardiovascular disease from that time can then be assessed based on a comparison between the baseline rate of increase in heart rate measurement and the measurement taken at the relevant testing time. As indicated above, a predetermined reference measurement may also be utilised which is derived from normative data of individuals matched for age, sex, weight, body mass index, smoking status, etc.

The inventor has shown that a less rapid increase in heart rate during the sub-maximal physical activity is associated with a worse performance by the individual in a subsequently performed athletic activity. Accordingly, the slower the rate of increase in heart rate of the individual during the sub-maximal physical activity compared to the predetermined reference measurement, the lower the recovery state of the individual, and/or the higher the likelihood the individual will subsequently perform the athletic activity below their optimal capacity. Conversely, a rate of increase in heart rate of the individual during the sub-maximal physical activity which is faster than the predetermined reference measurement indicates that the individual has fully recovered from the athletic activity, and/or indicates a higher likelihood that the individual will be able to subsequently perform the athletic activity above their optimal capacity. Furthermore, given that the rate of increase in heart rate of the individual is now faster than the reference measurement, it can be said that the individual has improved their fitness since the reference measurement was taken.

In circumstances where the rate of increase in heart rate of the individual during the sub-maximal physical activity is the same as the predetermined reference measurement, it also means that the individual has fully recovered from the athletic activity; however, it indicates that the individual has a higher likelihood of subsequently performing the athletic activity at their optimal capacity, rather than above their optimal.

As indicated above, the inventor has also found that the rate of increase in heart rate during sub-maximal exercise is also related to two recognised risk factors for cardiovascular disease, namely age and cardiorespiratory fitness (as indicated by performance during a 5 minute maximal exercise performance test). For example, the inventor has shown that the rate of increase in heart rate during sub-maximal exercise is inversely correlated with age (in years) and is positively correlated with maximal exercise performance (i.e. a marker of cardiorespiratory fitness). Accordingly, a slower rate of increase in heart rate of the individual during the sub-maximal physical activity compared to the predetermined reference measurement indicates that the risk of cardiovascular disease developing in the individual has increased from when the predetermined reference measurement was obtained. Furthermore, a slower rate of increase in heart rate of the individual during the sub-maximal physical activity compared to the predetermined reference measurement is also indicative of the progression of cardiovascular disease in the individual from when the predetermined reference measurement was obtained.

Conversely, a faster rate of increase in heart rate of the individual during the sub-maximal physical activity compared to the predetermined reference measurement indicates that the risk of cardiovascular disease developing in the individual has decreased, and is also indicative of an improvement of cardiovascular disease in the individual, from when the predetermined reference measurement was obtained.

The rate of increase in heart rate of the individual during the sub-maximal physical activity can be determined from heart rate measurements taken during the entire activity, or during a defined period of the activity, as described above. In one embodiment, the heart rate measurements may begin before a person commences the sub-maximal activity. For example, the heart rate is measured for a period of up to 30 seconds prior to commencing activity and for up to five minutes during the activity. The rate of increase in heart rate is then determined from the heart rate information obtained from that measurement time period, as described above.

The methods of the present invention, as described above, can be performed in any manner of means as would be understood by a person skilled in the art. For example, with reference to FIG. 1 there is shown an example device 100 for determining a recovery state of an individual according to a first aspect of the invention, for predicting an individual's physical performance capacity according to a second aspect of the invention, for determining a change in the risk of cardiovascular disease in an individual according to a third aspect of the invention, and/or for assessing the progression of cardiovascular disease in an individual according to a fourth aspect of the invention. The device 100 includes one or more heart rate transmitters 101a, 101b, 101c for detecting and measuring the heartbeat and heart rate of an individual, a processing unit 110 which is connected to the one or more heart rate transmitters 101a, 101b, 101c. The processing unit 110 receives and processes the heart rate information from the heart rate transmitters 101a, 101b, 101c. The processing unit 110 may include a processor 115 which includes a number of components for processing and computing various signals received from the one or more heart rate transmitters 101a, 101b, 101c or software to carry out these functions. These will be described further with reference to FIGS. 2a to 2e (hardware) and FIGS. 3-7 (software). The processing unit 110 also includes a memory 120 for storing data temporarily and running software. A database 125 is included for storing data from the processing unit 110. The processing unit 110 also preferably includes a display 130 for displaying data processed by the processor 115. It will be appreciated that the processing unit 110 may be a wrist type monitor in which, the user of the monitor can see the results via a display 130. Alternatively, or in addition to the display 130 the processing unit 110 may be connected to a personal computer 135. The personal computer may be directly connected to the processing unit 110 or may be connected over a network such as the internet so that the computer 135 may be at a remote location.

Means for detecting and measuring the heartbeat and heart rate of the individual are known in the art. Typically, the methods and devices of the present invention employ a heart rate monitor 100 to measure heart rate. Heart rate monitors are commercially available as would be known to the skilled person. As will be described in more detail below, a heart rate monitor typically includes one or more heart rate transmitters 101a, 101b, 101c for detecting the heart beat of the individual, and a processing unit 110 (e.g. a wrist device) which receives and processes the heart rate information from the transmitter.

As well as measuring heart rate, the heart rate monitor 100 may also be adapted to determine the rate of increase in heart rate of the individual, including the maximal or average rate of increase. In this regard, the one or more transmitters 101a, 101b, 101c may communicate with the associated processing unit 110, which receives the heart rate information from the one or more transmitters 101a, 101b, 101c and processes this information via encoded instructions to determine the rate of increase in heart rate. As described below, with reference to FIGS. 2a to 2e, the heart rate monitor 100 may also be adapted to determine the rate of increase in heart rate, and may also have the ability to compare the rate of increase in heart rate to the predetermined reference measurement. Still further, the monitor may be adapted to determine and display the recovery state of the individual and/or a performance ability prediction. However, it will be clearly understood that any one or more of these parameters may be determined manually, for example by the individual themselves after completion of their sub-maximal physical activity, or by an independent party such as their coach or physician either during or after the sub-maximal activity. One or more of the parameters may also be determined by an independent device such as by a computer situated remotely, such as a personal computer 135.

As shown in FIGS. 2a to 2e, the processing unit 110 includes a processor 115 which may include dedicated hardware modules or units to carry out hardcoded instructions and provide information to determine the physical recovery and physical performance capacity of an individual. However, it will be appreciated that these modules need not be necessarily implemented in hardware but may be implemented in purely in software which is stored on memory 120 and carried out by the processor 115. This will be described with reference to FIGS. 3 to 7.

According to a fifth aspect of the present invention, there is provided a device for determining a recovery state of an individual from an athletic activity. As shown in FIG. 2a, the processor 115 may include dedicated hardware modules or units including a heart rate measurement unit 140 which measures the heart rate of the individual (via the one or more heart rate transmitters 101a, 101b and 101c) during a period of sub-maximal physical activity. Also provided is a rate of increase in heart rate determination unit 145 which determines the rate of increase in heart rate of the individual during the sub-maximal physical activity. A comparison unit 150 is also provided for performing a comparison between the determined rate of increase in heart rate of the individual and a predetermined reference measurement. The predetermined reference measurement may be stored in memory 120 or on a database 125 of the monitor 110 and accessed as required by processor 115. Finally, the processor 115 includes a recovery state determination unit 155 which determines the recovery state of the individual from the athletic activity on the basis of the comparison (as determined by the comparison unit 150).

According to a sixth aspect of the present invention, there is provided a device for predicting an individual's ability to perform an athletic activity at, above, or below, their optimal capacity. FIG. 2b shows the processor 115 including a module for predicting an individual's ability to perform an athletic activity at, above, or below, their optimal capacity. As described with reference to FIG. 2a, the processor 115 includes a heart rate measurement unit 140 for measuring a heart rate of the individual during a sub-maximal physical activity, a rate of increase in heart rate determination unit 145 for determining the rate of increase in the heart rate of the individual during the sub-maximal physical activity, and a comparison unit 150 which performs a comparison between the determined rate of increase in heart rate of the individual and a predetermined reference measurement. Finally, the processor 115 includes a prediction determination unit 160 for predicting the individual's ability to perform the athletic activity at, above, or below, their optimal capacity on the basis of the comparison determined by the comparison unit 150. The prediction determination unit 160 may be an additional component to the recovery state determination unit 155 present in the processor 115, or may replace the recovery state determination unit 155 in the processor 115.

According to a seventh aspect of the present invention, there is provided a device for determining a change in the risk of cardiovascular disease developing in an individual. FIG. 2c shows the processor 115 including a module for determining a change in the risk of cardiovascular disease developing in an individual. As described with reference to FIG. 2a, the processor 115 includes a heart rate measurement unit 140 for measuring a heart rate of the individual during a sub-maximal physical activity, a rate of increase in heart rate determination unit 145 for determining the rate of increase in the heart rate of the individual during the sub-maximal physical activity, and a comparison unit 150 which performs a comparison between the determined rate of increase in heart rate of the individual and a predetermined reference measurement. Finally, the processor 115 includes a cardiovascular disease risk determination unit 165 for determining a change in the risk of cardiovascular disease developing in the individual on the basis of the comparison determined by the comparison unit 150. The cardiovascular disease risk determination unit 165 may be an additional component to the recovery state determination unit 155 and the prediction determination unit 160 present in the processor 115, or may replace either or both of the recovery state determination unit 155 and prediction determination unit 160 in the processor 115.

According to an eighth aspect of the present invention, there is provided a device for assessing the progression of cardiovascular disease in an individual. FIG. 2d shows the processor 115 including a module for assessing the progression of cardiovascular disease in an individual. As described with reference to FIG. 2a, the processor 115 includes a heart rate measurement unit 140 for measuring a heart rate of the individual during a sub-maximal physical activity, a rate of increase in heart rate determination unit 145 for determining the rate of increase in the heart rate of the individual during the sub-maximal physical activity, and a comparison unit 150 which performs a comparison between the determined rate of increase in heart rate of the individual and a predetermined reference measurement. Finally, the processor 115 includes a cardiovascular disease progression assessment unit 170 for assessing the progression of cardiovascular disease in the individual on the basis of the comparison determined by the comparison unit 150. The cardiovascular disease progression assessment unit 170 may be an additional component to the recovery state determination unit 155, the prediction determination unit 160, and the cardiovascular disease risk determination unit 165 present in the processor 115, or may replace any one or more of the recovery state determination unit 155, the prediction determination unit 160, and the cardiovascular disease risk determination unit 165, in the processor 115.

The heart rate measurement unit 140 measures the individual's heart rate during a defined period of the sub-maximal physical activity, as described above. The individual's heart rate can be measured in a number of ways as would be understood by the skilled person. For example, if the device 100 is a heart rate monitor, as described above, the monitor will include one or more heart rate transmitters 101a, 101b, 101c that are generally positioned around the individual's chest. The one or more transmitters 101a, 101b, 101c include electrodes that detect the electric potential difference generated by the electrical activity of the heart muscle as it beats. This generates an electrocardiogram (ECG) signal characterising the electrical activity of the heart muscle. The ECG is typically fed to an ECG preamplifier from the electrodes. The preamplifier serves to amplify the ECG signal which is then transmitted telemetrically, optically or galvanically to a processing unit 110.

The heart rate monitor 100 may also be in the form of a wearable garment (not shown) which incorporates flexible electronics. In this regard, the garment may include textile-based sensors that are woven into the fabric of the garment, and which are in contact with the skin of the individual. The sensors essentially perform the functions of the electrodes described above which are part of the one or more heart rate transmitters 101a, 101b, 101c of a typical heart rate monitor 100. Examples of such garments and associated flexible electronics are those which are produced commercially, for example by companies such as Textronics, VivoMetrics and Sensatex.

The processing unit 115 may be present in a device attached to the individual, such as a wrist device positioned around the individual's wrist, or may be attached to the individual's exercise equipment, such as their bicycle, as they complete their sub-maximal physical activity. However, the processing unit 115 need not be located on, or with, the individual. For example, the processing unit may be located remote from the individual, such as on, or with, the individual's trainer or coach as they monitor the individual. The processing unit may be implemented by using analogue circuits, an application specific integrated circuit, a digital processor, memory, and computer software as would be understood by the skilled person.

The processing unit 115 may include the rate of increase in heart rate determination unit 145. The determination unit 145 will determine the rate of increase in heart rate of the individual during the sub-maximal physical activity based on the heart rate measurements. The determination unit 145 is able to process the heart rate information it receives via encoded instructions to determine the rate of increase in heart rate.

Information generated by the determination unit 145 feeds a comparison unit 150 which then performs a comparison between the rate of increase in heart rate of the individual, as determined by the determination unit 145, and the predetermined reference measurement. The comparison unit 150 may then communicate with the recovery state determination unit 155, the prediction determination unit 160, the cardiovascular disease risk determination unit 165, and/or the cardiovascular disease progression assessment unit 170, which proceeds to process the derived comparison information to determine a recovery state of the individual, to produce a prediction of the individual's ability to perform an athletic activity at, above, or below, their optimal capacity, to determine a change in the risk of cardiovascular disease developing in the individual, and to assess the progression of cardiovascular disease in the individual, respectively. For example, the recovery state determination unit 155, the prediction determination unit 160, the cardiovascular disease risk determination unit 165, and the cardiovascular disease progression assessment unit 170 may have the ability to execute a computer process according to an appropriate encoded algorithm which converts the rate of increase in heart rate comparison information into a recovery state value, a performance ability prediction, a cardiovascular disease risk value, or a cardiovascular disease progression value, respectively.

The resultant values or predictions may be communicated to the individual in any number of ways. For example, the device may include a display unit that may display the recovery state (as a liquid crystal readout for example) in a numerical or graphical manner, such as in the form of a percentage of complete recovery or percent performance ability, a value out of 10 or 100 etc, or in character format, such as "full recovery", "partial recovery", and like terms. The display unit may also display the change in cardiovascular disease risk value and/or the cardiovascular disease progression in the form of a percentage increase or decrease, or in character format, such as "higher risk", "lower risk" or "no change", and like terms.

In embodiments of the invention, the methods and devices described herein are used to determine exercise instructions for the individual. As indicated previously, the effect of over-reaching or over-training may be detrimental to their performance and may even have an adverse effect on the health of the individual, particularly where the individual is at risk of developing cardiovascular disease, or indeed already suffers from cardiovascular disease. Therefore, being able to tailor the individual's training or exercise program based on their physical condition prior to conducting an athletic activity is very useful.

The exercise instruction information will take into account the determined recovery state of the individual, the prediction of the ability of the individual to perform an athletic activity at, above, or below, their optimal capacity, the risk of cardiovascular disease developing in the individual, and/or the progression of cardiovascular disease in the individual. For example, if the rate of increase in heart rate of the individual during the sub-maximal physical activity has been determined to be slower than the predetermined reference value (i.e. the individual has not fully recovered, is predicted to be unable to perform at, or above, their optimal capacity, has an increased risk of developing cardiovascular disease, and/or cardiovascular disease has progressed in the individual), the individual may decide, be instructed by their coach or physician, or otherwise be encouraged, to do light exercise or have a rest day to promote recovery. Conversely, if the methods and devices of the present invention determine that the individual is close to, or at, full recovery, has a decreased risk of developing cardiovascular disease, and/or cardiovascular disease has improved, the individual may decide, be instructed by their coach or physician, or otherwise be encouraged, to do heavier exercise such that the exercise will lead to a positive build-up of performance and physical condition, or in some circumstances indeed be safe to conduct. Alternatively, if the rate of heart rate increase is slow and an individual has not been training this would inform that the individual is losing fitness and additional training is required in order to return to optimal training capacity. The intensity of the exercise instructions will therefore be dictated by the determined rate of increase in heart rate and the comparison to the predetermined reference measurement. A representation of the nature of the exercise instructions is described in more detail below.

The present invention also provides a method of determining exercise instructions for an athletic activity for an individual, the method including:
(a) subjecting the individual to a sub-maximal physical activity prior to the athletic activity;
(b) measuring the heart rate of the individual during the sub-maximal physical activity;
(c) determining the rate of increase in heart rate of the individual during the sub-maximal physical activity;
(d) performing a comparison between the determined rate of increase in heart rate of the individual and a predetermined reference measurement; and
(e) determining exercise instructions for the athletic activity on the basis of the comparison.

Details on how each of steps (a) to (e) can be performed have been described above.

Furthermore, the present invention provides a device for determining exercise instructions for an athletic activity for an individual. FIG. 2e shows the processor 115 including the additional component for determining exercise instructions for an athletic activity for an individual. As noted above with reference to FIGS. 2a to 2d, the processor 115 includes a heart rate measurement unit 140 for measuring the heart rate of the individual during a sub-maximal activity conducted prior to the athletic activity, a rate of increase in heart rate determination unit 145 for determining the rate of increase in heart rate of the individual during the sub-maximal physical activity, and a comparison unit 150 for performing a comparison between the determined rate of increase in heart rate of the individual and a predetermined reference measurement. The processor 115 includes the additional component 175 of an exercise instruction determination unit for determining exercise instructions for the athletic activity on the basis of the comparison.

Details on how each of steps (a) to (c) can be performed have been described above.

The comparison unit 150 can communicate with the exercise instruction determination unit 175 which determines exercise instruction information for the individual for at least one future athletic activity. The exercise instruction information may be communicated to the individual in any number of ways, as described above for the display of the recovery state value, the performance ability prediction, the cardiovascular disease risk value, and the cardiovascular disease progression value. The exercise instruction information will advise the individual, their coach, trainer or physician, what the nature of the subsequent athletic activity should be. For example, there may be a recommendation as to the intensity of the activity, the duration of the activity, the heart rate range required for the activity, or indeed a recommendation that the individual rest completely.

If the comparison unit 150 determines that the rate of increase in heart rate of the individual during the sub-maximal physical activity is slower than the predetermined reference measurement, the exercise instruction determination unit 175 will determine exercise instructions for the athletic activity on the basis that the individual is likely to perform the athletic activity below their optimal capacity, that there is an increased risk of cardiovascular disease developing in the individual, and/or that cardiovascular disease has progressed in the individual. In this instance, the exercise instruction determination unit might determine the exercise instruction to be REST, LIGHT EXERCISE or MODERATE INTENSITY EXERCISE, for example if the training history of the individual indicates that they have been undertaking a lot of training and are potentially becoming overreached or overtrained. Alternatively, the exercise instruction determination unit 175 might determine the exercise instruction to be MODERATE INTENSITY EXERCISE or HIGH INTENSITY EXERCISE, for example if the training history of the individual indicates that there has been little exercise training such that the individual is potentially losing fitness.

Similarly, if the comparison unit 150 determines that the rate of increase in heart rate of the individual during the sub-maximal physical activity is faster than, or identical to, the predetermined reference measurement, the exercise instruction determination unit 175 will determine exercise instructions for the athletic activity on the basis that the individual is capable of performing the athletic activity above, or at, respectively, their optimal capacity, or for example that the risk of cardiovascular disease developing in the individual has decreased. In this instance, the exercise instruction determination unit 175 might determine the exercise instruction to be MODERATE INTENSITY EXERCISE or HEAVY EXERCISE.

Each exercise instruction may be associated with a target variable that can be measured with the device 100, and which can characterise the target of the exercise numerically. For example, the aforementioned exercise instructions may be associated with the target average heart rate as follows: LIGHT: average heart rate of about 65-74% of maximum heart rate of the individual; MODERATE: average heart rate of about 75-84% of maximum heart rate; and HEAVY: average heart rate of about 85% of maximum heart rate or greater.

Figure 3:
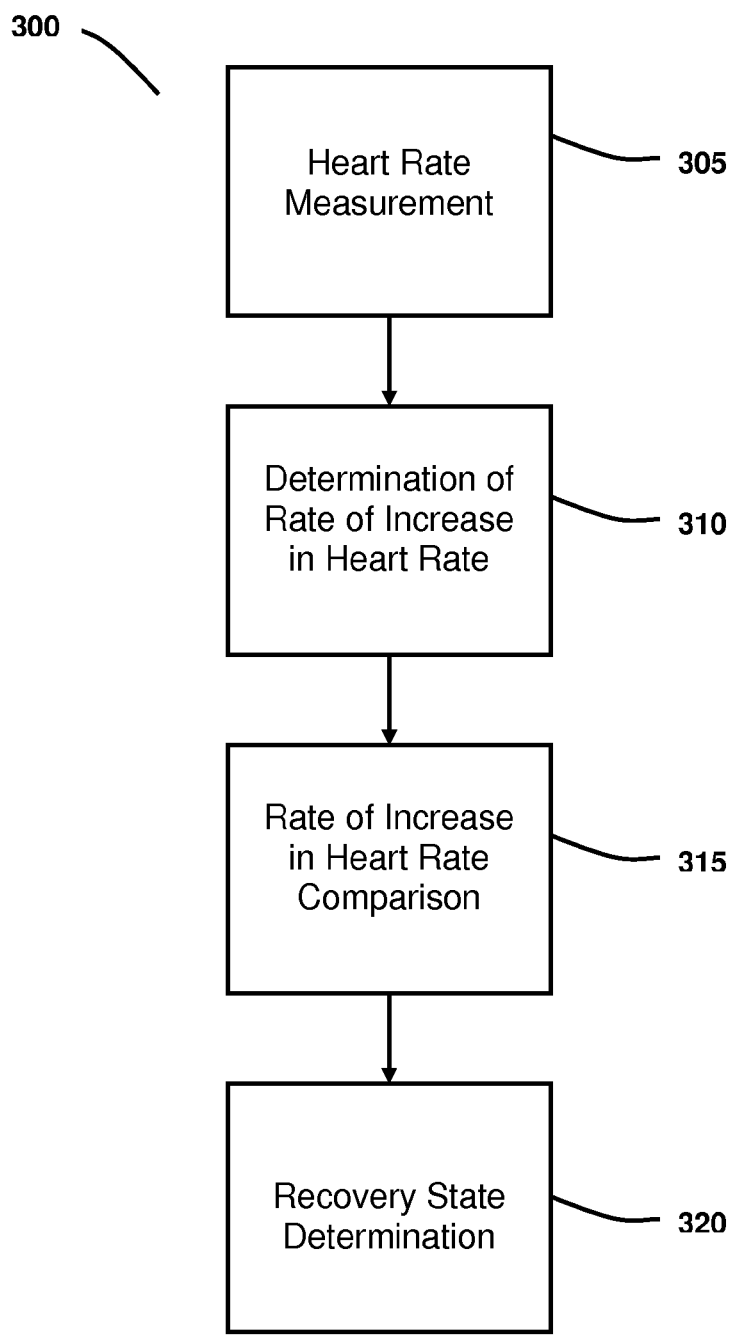
FIG. 3 is a flow diagram of a method for determining a recovery state of an individual from athletic activity according to an embodiment of the invention.

The hardware modules or units described with reference to FIGS. 2a to 2e may also be implemented in software running in memory. FIG. 3 describes a method 300 of the invention for determining the recovery state of an individual from an athletic activity. At step 305 a heart rate measurement is received from an individual during a sub-maximal physical activity conducted prior to the athletic activity. This may be via one or more heart rate transmitters 101a, 101b and 101c and a processing unit 110 as discussed with reference to FIG. 1. Control then moves to step 310 where the rate of increase in heart rate of the individual during the sub-maximal physical activity is determined. This step may be carried out by the processor 115 on the processing unit 110. Control then moves to step 315 where a comparison between the determined rate of increase in heart rate of the individual (determined at step 310) together with a predetermined reference measurement are compared. The comparison may be carried out by the processor 115 on the processing unit 110. The predetermined reference measurement may be stored in the database 125 and/or memory 120 of the processing unit 110. Finally, at step 320 the recovery state of the individual from the athletic activity is determined on the basis of the comparison determined at step 315. The results may then be optionally displayed on the display 130 of the processing unit 110, or alternatively on a display associated with a personal computer 135.

Figure 4:
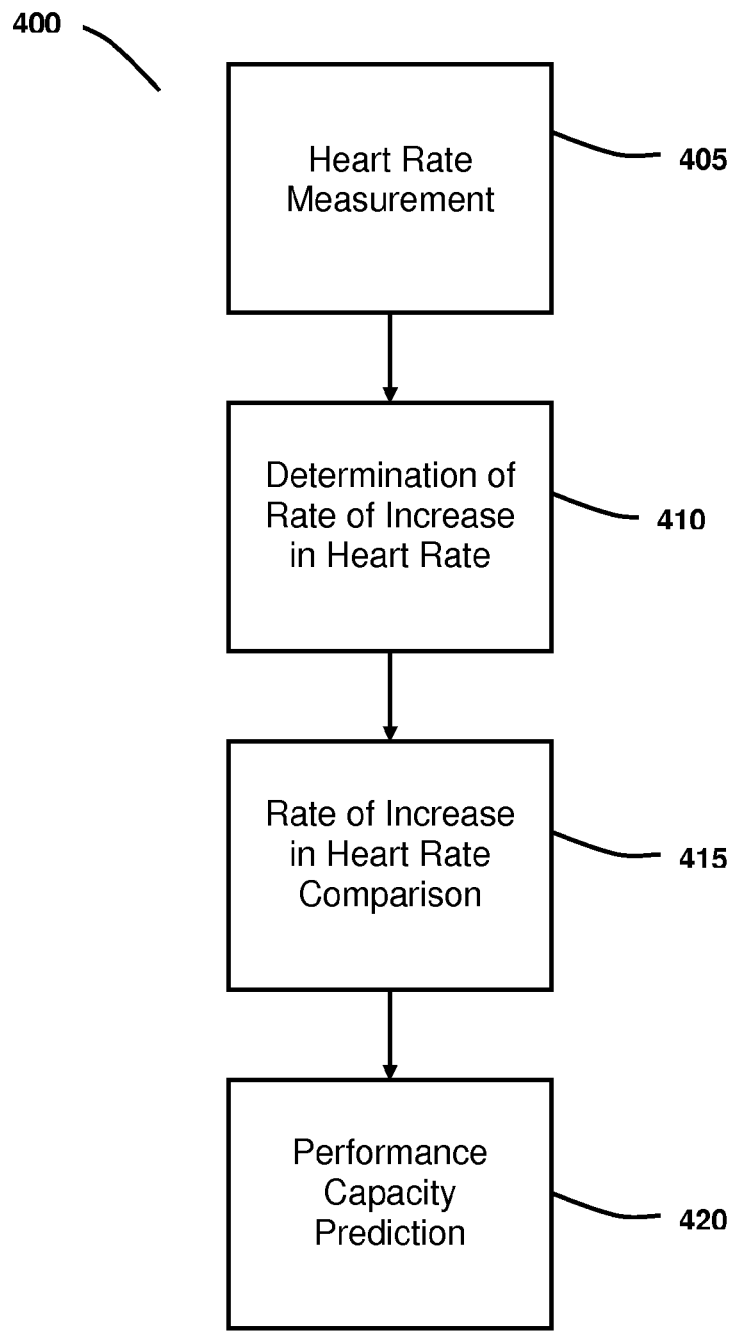
FIG. 4 is a flow diagram of a method of predicting an individual's ability to perform an athletic activity at, above, or below, their optimal capacity according to another embodiment of the invention.

FIG. 4 describes a method 400 of predicting an individual's ability to form an athletic activity at, above, or below, their optimal capacity. At step 405 a heart rate measurement is received from an individual during a sub-maximal physical activity conducted prior to the athletic activity. This may be via one or more heart rate transmitters 101a, 101b and 101c and a processing unit 110 as discussed with reference to FIG. 1. Control then moves to step 410 where the rate of increase in heart rate of the individual during the sub-maximal physical activity is determined. This step may be carried out by the processor 115 on the processing unit 110. Control then moves to step 415 where a comparison between the determined rate of increase in heart rate of the individual (determined at step 410) together with a predetermined reference measurement are compared. The comparison may be carried out by the processor 115 on the processing unit 110. The predetermined reference measurement may be stored in the database 125 and/or memory 120 of the processing unit 110. Finally, at step 420 the individual's ability to perform the athletic activity at, above, or below, their optimal capacity is predicted on the basis of the comparison determined at step 415. The results then may be optionally displayed on display 130 of the processing unit 110 or alternatively on a display associated with a personal computer 135.

Figure 5:
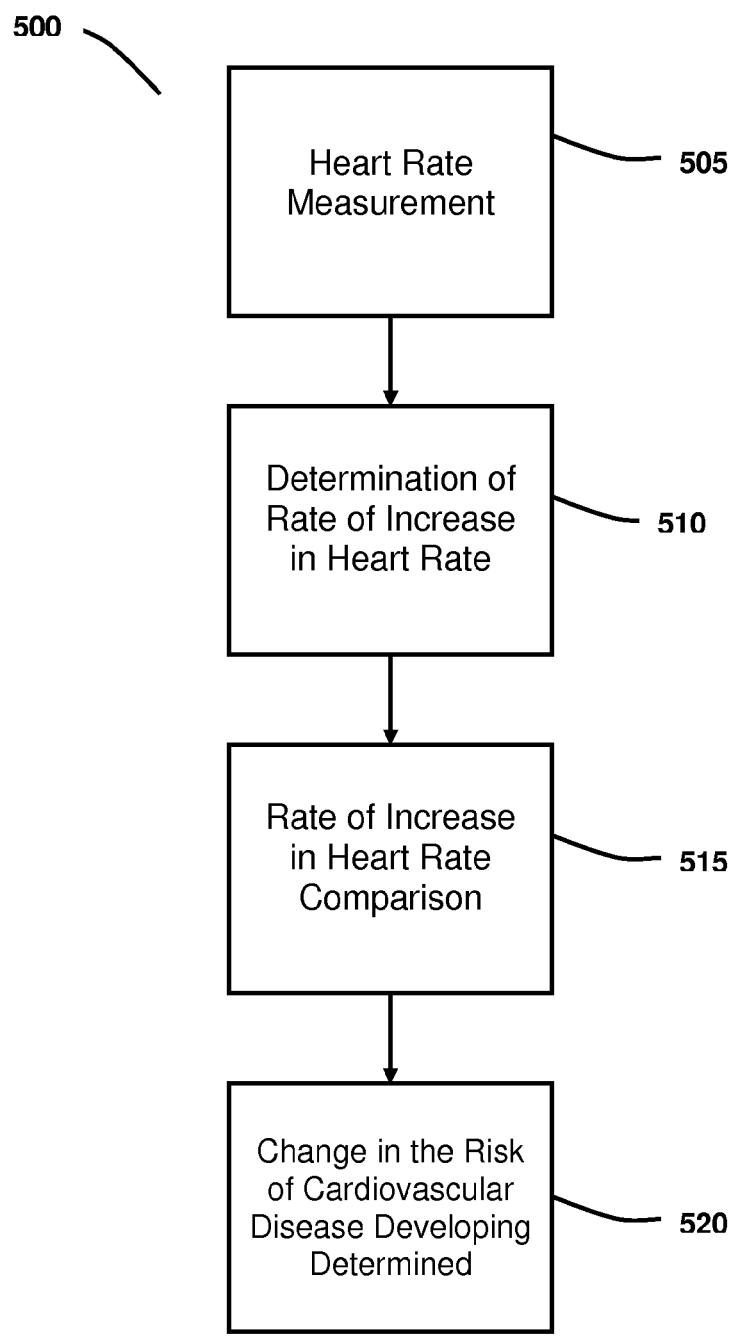
FIG. 5 is a flow diagram of a method of determining a change in the risk of cardiovascular disease developing in an individual according to another embodiment of the invention.

FIG. 5 describes a method 500 of determining a change in the risk of cardiovascular disease developing in an individual. At step 505 a heart rate measurement is received from an individual during a sub-maximal physical activity conducted prior to the athletic activity. This may be via one or more heart rate transmitters 101a, 101b and 101c and a processing unit 110 as discussed with reference to FIG. 1. Control then moves to step 510 where the rate of increase in heart rate of the individual during the sub-maximal physical activity is determined. This step may be carried out by the processor 115 on the processing unit 110. Control then moves to step 515 where a comparison between the determined rate of increase in heart rate of the individual (determined at step 510) together with a predetermined reference measurement are compared. The comparison may be carried out by the processor 115 on the processing unit 110. The predetermined reference measurement may be stored in the database 125 and/or memory 120 of the processing unit 110. Finally, at step 520 the change in the risk of cardiovascular disease developing in the individual is determined on the basis of the comparison obtained at step 515. The results then may be optionally displayed on display 130 of the processing unit 110 or alternatively on a display associated with a personal computer 135.

Figure 6:
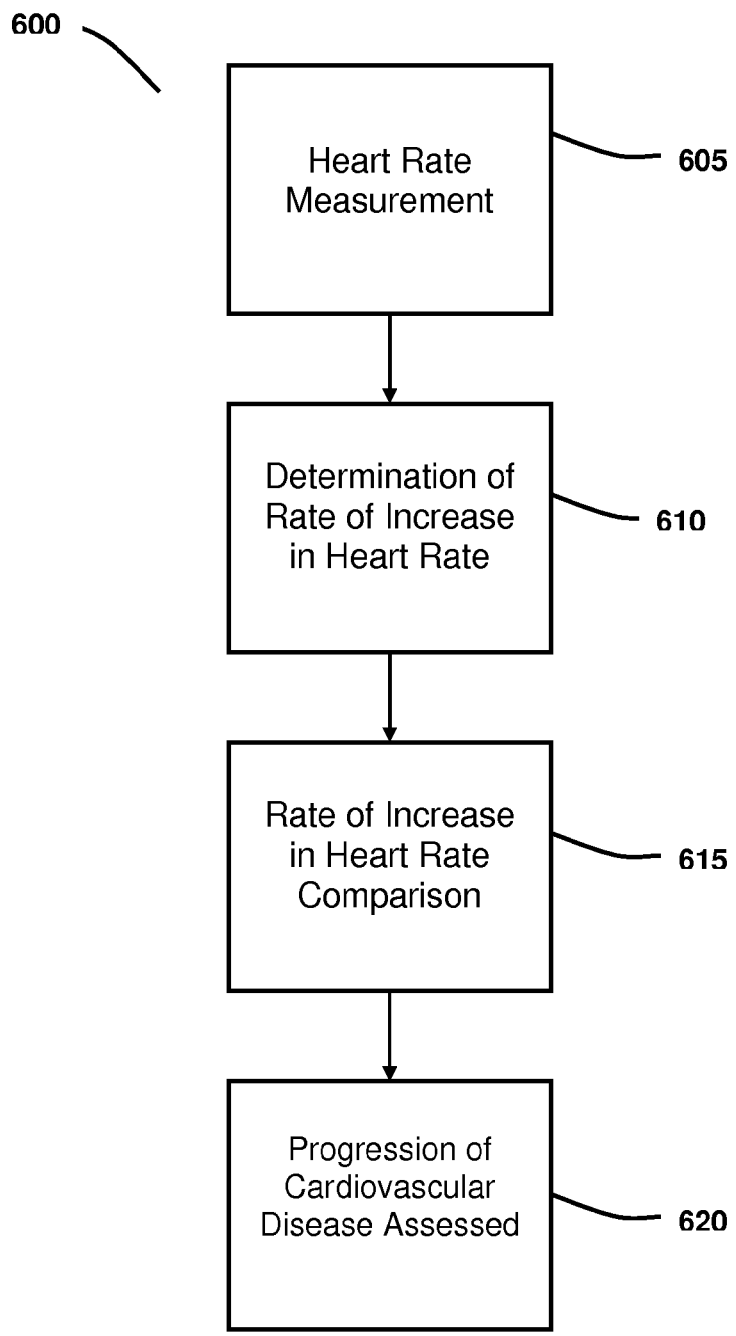
FIG. 6 is a flow diagram of a method of assessing the progression of cardiovascular disease in an individual according to another embodiment of the invention.

FIG. 6 describes a method 600 of assessing the progression of cardiovascular disease in an individual. At step 605 a heart rate measurement is received from an individual during a sub-maximal physical activity conducted prior to the athletic activity. This may be via one or more heart rate transmitters 101a, 101b and 101c and a processing unit 110 as discussed with reference to FIG. 1. Control then moves to step 610 where the rate of increase in heart rate of the individual during the sub-maximal physical activity is determined. This step may be carried out by the processor 115 on the processing unit 110. Control then moves to step 615 where a comparison between the determined rate of increase in heart rate of the individual (determined at step 610) together with a predetermined reference measurement are compared. The comparison may be carried out by the processor 115 on the processing unit 110. The predetermined reference measurement may be stored in the database 125 and/or memory 120 of the processing unit 110. Finally, at step 620 the progression of cardiovascular disease in the individual is assessed on the basis of the comparison obtained at step 615. The results then may be optionally displayed on display 130 of the processing unit 110 or alternatively on a display associated with a personal computer 135.

Figure 7:
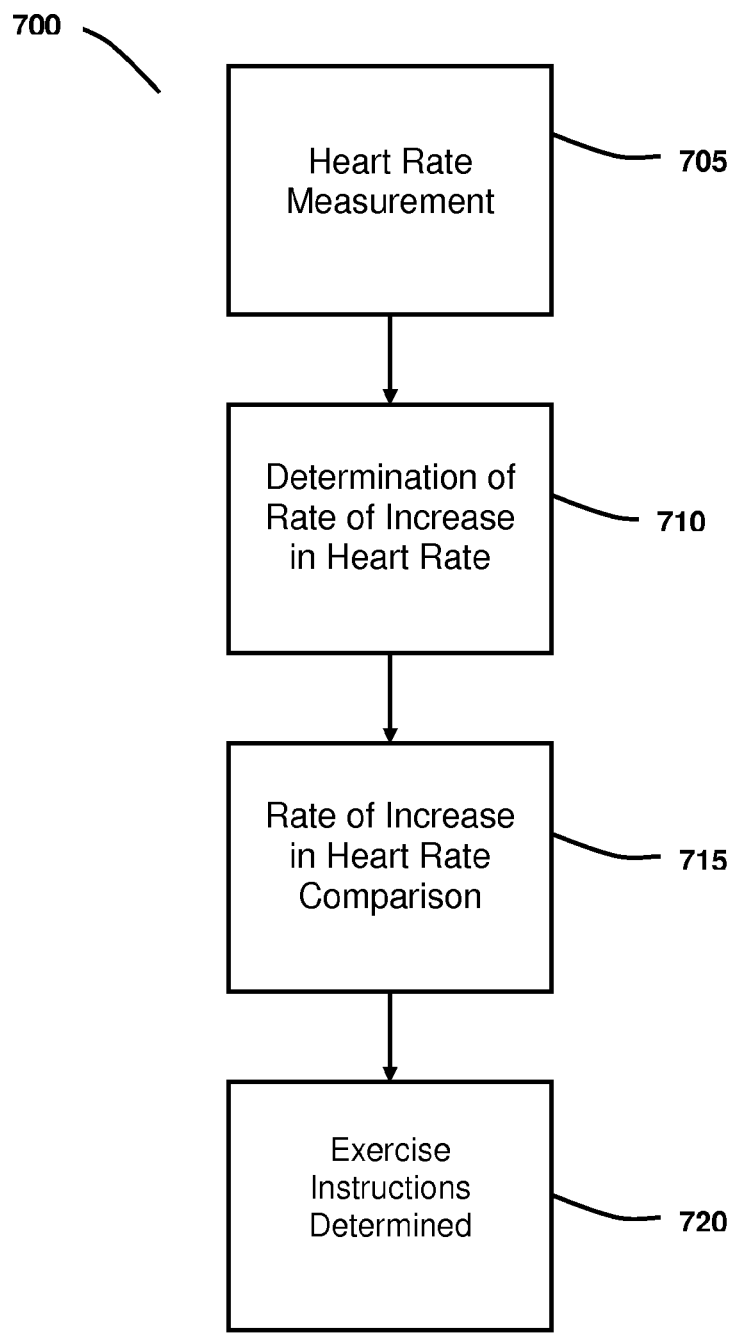
FIG. 7 is a flow diagram of a method for determining exercise instructions for an athletic activity for an individual according to another embodiment of the invention.

FIG. 7 is a method 700 for determining exercise instructions for an athletic activity for an individual. At step 705 a heart rate measurement is received from an individual during a sub-maximal physical activity conducted prior to the athletic activity. This may be via one or more heart rate transmitters 101a, 101b and 101c and processing unit 110 as discussed with reference to FIG. 1. Control then moves to step 710 where the rate of increase in heart rate of the individual during the sub-maximal physical activity is determined. This step may be carried out by the processor 115 on the processing unit 110. Control then moves to step 715 where a comparison between the determined rate of increase in heart rate of the individual (determined at step 710) together with a predetermined reference measurement are compared. The comparison may be carried out by the processor 115 on the processing unit 110. The predetermined reference measurement may be stored in the database 125 and/or memory 120 of the processing unit 110. Finally, at step 720 exercise instructions for the athletic activity on the basis of the comparison in step 715 are determined. The results then may be optionally displayed on display 130 of processing unit 110 or alternatively on a display associated with a personal computer 135.

The present invention also provides a computer software product, including coded instructions for executing a computer process in a digital processor, wherein the computer process determines any one or more of the following:
(1) a recovery state of an individual from an athletic activity;
(2) a prediction as to an individual's ability to perform an athletic activity at, above, or below, their optimal capacity;
(3) a change in the risk of cardiovascular disease developing in an individual;
(4) progression of cardiovascular disease in an individual; and
(5) exercise instructions for an athletic activity for an individual.

The computer process may be included in the encoded instructions executed in the processing unit and/or determination unit of the device, as described above. The encoded instructions may be included in a computer software product and they may be transferred via a distribution means. The distribution means may be for example an electric, magnetic or optical means. The distribution means may also be a physical means, such as a memory unit, an optical disc or a telecommunication signal.

As described above, the rate of increase in heart rate of an individual as measured during a sub-maximal physical activity serves as a marker for the physical condition of an individual. Accordingly, the marker may be used to determine a recovery state of an individual from an athletic activity, predict an individual's ability to perform an athletic activity at, above, or below, their optimal capacity, determine a change in the risk of cardiovascular disease developing in an individual, and/or assess the progression of cardiovascular disease in an individual, using the methods and devices as described in detail above.

The present invention provides a number of advantages over current physical condition testing systems. For example, it provides an objective test for determining the physical recovery state of an individual, for predicting the individual's ability to perform an athletic activity, for determining a change in the risk of developing cardiovascular disease, and/or for assessing progression of cardiovascular disease, which does not require the individual to undergo a maximal exercise performance test to exhaustion. In fact, the present invention requires that the individual need only perform a (sub-maximal) warm-up activity for the assessment to be made, and therefore no disruption to their usual routine is needed. Furthermore, the warm-up activity can be of a non-prescribed or prescribed workload. The methods and devices according to the present invention are also non-invasive in nature and require as little as 30 seconds to five minutes of measurement time. In addition, they do not require the provision of expensive equipment to conduct the tests. Therefore, the present invention provides a simple, quick and inexpensive means for measuring the physical recovery, physical performance capacity, change in cardiovascular disease risk, progression of cardiovascular disease, and/or exercise instructions for an individual.

As used in this specification, the singular forms "a", an and "the" include plural aspects unless the context clearly dictates otherwise.

"About" as used in the specification means approximately or nearly and in the context of a numerical value or range set forth herein means±10% of the numerical value or range recited or claimed.

Where a range of values is expressed, it will be clearly understood that this range encompasses the upper and lower limits of the range, and all values in between these limits.

Although the invention has been described with reference to an "individual" (i.e. a human subject), it is to be clearly understood that the methods and devices as described and claimed herein are not to be limited in their use to humans. For example, the methods and devices of the invention can also be used on animals, including those animals which are involved in competitive activities (e.g. horses and greyhounds).

The range of applications in humans to which the present invention may be applied is also not to be limited. Therefore, the present invention may find use in applications including fitness, sports, medical health care for monitoring patients with cardiovascular disease, military use (for example training), lifestyle health for determining risk of developing cardiovascular disease, corporate/professional wellness, or facilitation of independent living by the elderly or sick.

The invention is further described in detail by reference to the following experimental examples. These examples are provided for purposes of illustration only, and are not intended to be limiting unless otherwise specified. Thus, the invention encompasses any and all variations which become evident as a result of the teaching provided herein.

EXAMPLE 1

Measurement of the Rate of Increase in Heart Rate in Competitive Male Triathletes and Cyclists Eight competitive male triathletes performed a 5-minute steady-state warm-up on an electrically-braked cycle ergometer at a self-selected (i.e. non-prescribed) sub-maximal exercise intensity and at prescribed sub-maximal exercise intensities of 100, 125, 150, 175 and 200 Watts. Heart rate was monitored every 1 second during the 30 seconds prior to commencing the sub-maximal exercise and throughout the 5 minutes of the sub-maximal exercise using a personal heart rate monitor. The heart rate was allowed to return to pre-exercise levels between each workload. After completing the sub-maximal exercise the triathletes performed a 5 minute maximal exercise test on the same electrically-braked cycle ergometer during which they performed as much work (kilojoules per kilogram of body mass) as they could.

A single triathlete then returned to the laboratory one week later and repeated the sub-maximal exercise at 100 Watts and at a self-selected workload, followed by a 5 minute maximal exercise test on the same cycle ergometer as used previously. This individual then ran for 2 hours on a treadmill at an exercise intensity that elicited 75% of their maximal heart rate. Following this treadmill run the individual was allowed to rest for approximately 1 hour until their heart rate had almost returned to its resting level. The individual then repeated the sub-maximal exercise at 100 Watts and at a self-selected workload and the 5 minute maximal cycle exercise test.

Sigmoidal curves (4 parameter) were fit to model the heart rate response during the rest period and the sub-maximal warm-ups. In this example, the maximal rate of increase in heart rate was identified during the sub-maximal exercise workloads by determining the maximal value for the first-derivative of the curve. However, it will be clearly understood that other equations may be fit to determine the rate of heart rate increase, and that the average rate of heart rate increase (as opposed to the maximal rate of heart rate increase) can also be used to predict the physiological readiness to perform and the recovery state. Indeed, the results obtained when the maximal and average rate of heart rate increase was used provided similar results.

Table 1 below provides data establishing the relationship between work done (kilojoules per kilogram of body mass) during the five minute maximal cycling time trial and the rate of increase in heart rate during 30 seconds of rest followed by various sub-maximal exercise workloads.

TABLE 1

| Sub-maximal Workload | Coefficient of Determination ($r^2$) | p-value |
|---|---|---|
| Self selected | 0.69 | 0.01 |
| 100 Watts | 0.80 | 0.003 |
| 125 Watts | 0.45 | 0.07 |
| 150 Watts | 0.69 | 0.01 |
| 175 Watts | 0.53 | 0.04 |
| 200 Watts | 0.80 | 0.003 |

Figure 8:
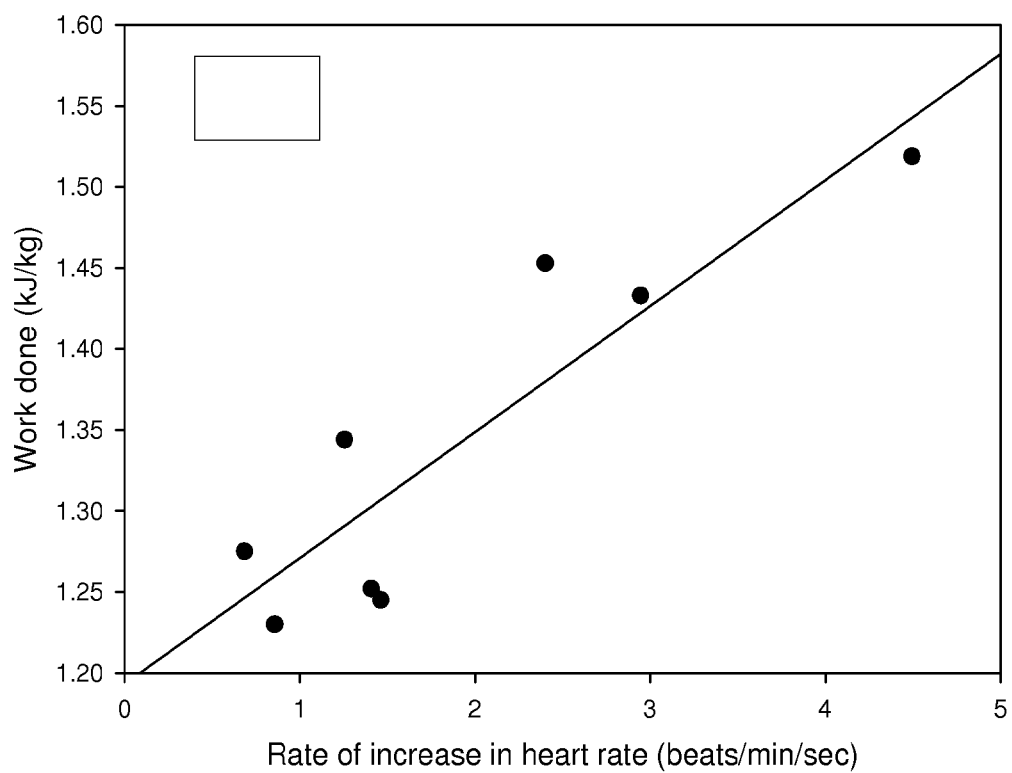
FIG. 8 is a graph showing the relationship between the rate of increase in heart rate in competitive male triathletes during 30 seconds of rest followed by 5 minutes of sub-maximal exercise at a workload of 100 Watts, and the work done during a subsequent five minute maximal cycling time trial.
Figure 9:
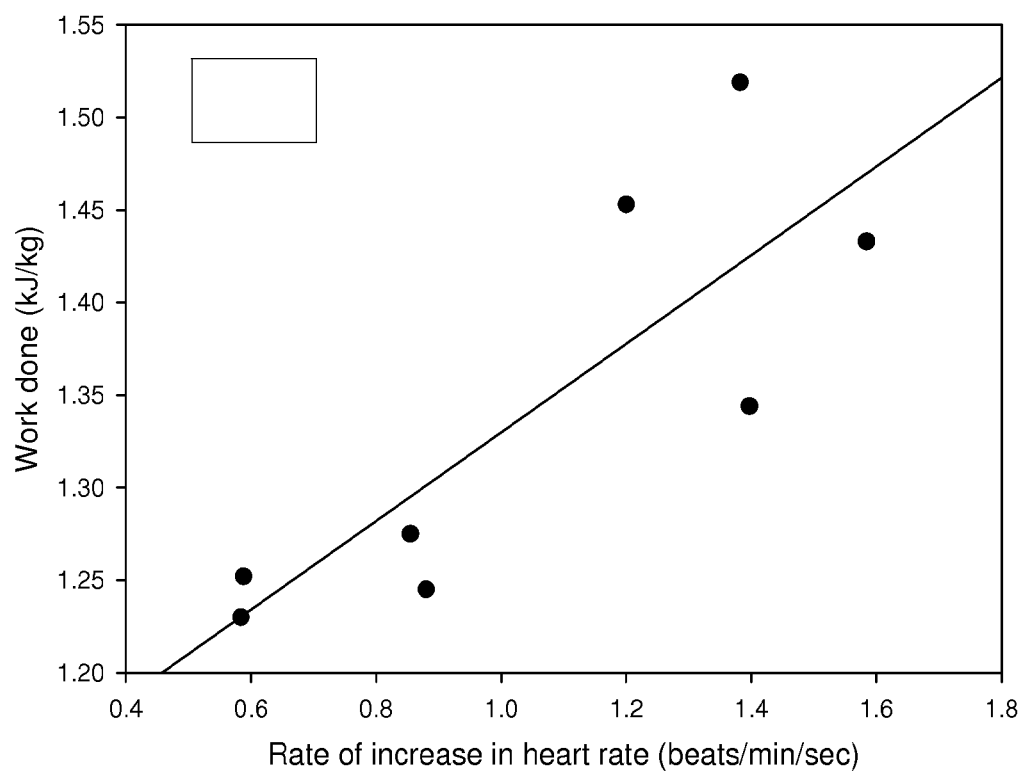
FIG. 9 is a graph showing the relationship between the rate of increase in heart rate in competitive male triathletes during 30 seconds of rest followed by 5 minutes of sub-maximal exercise at a self-selected steady state warm up, and the work done during a subsequent five minute maximal cycling time trial.
Figure 10:
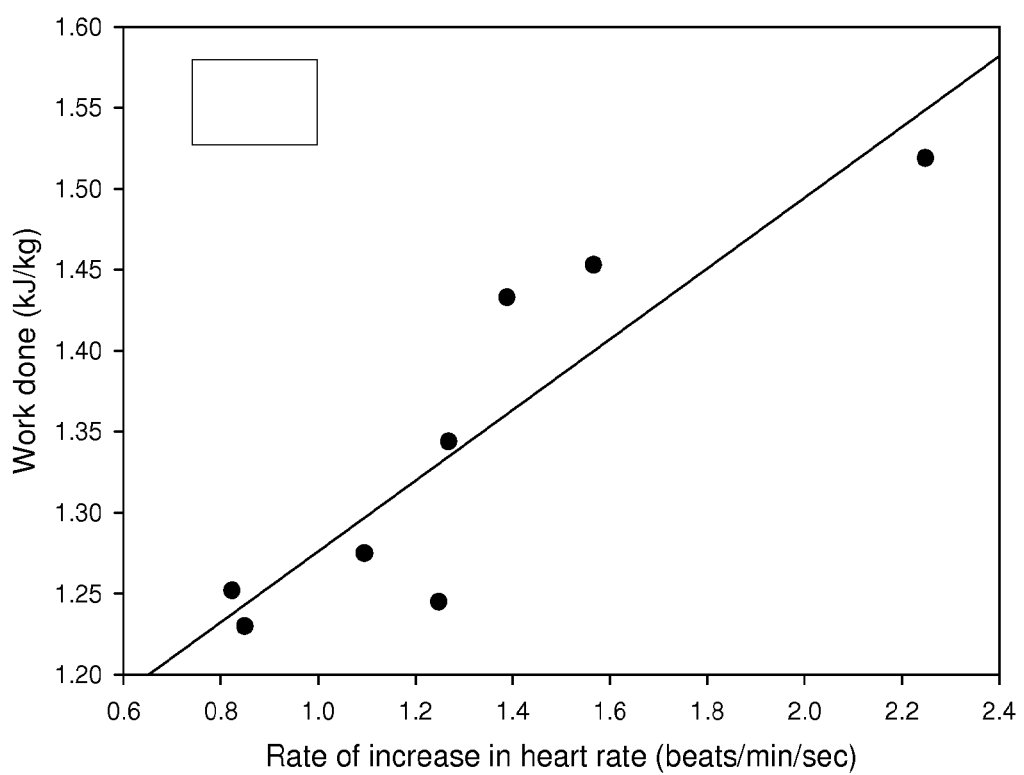
FIG. 10 is a graph showing the relationship between the rate of increase in heart rate in competitive male triathletes during 30 seconds of rest followed by 5 minutes of sub-maximal exercise at a workload of 200 Watts, and the work done during a subsequent five minute maximal cycling time trial.

As can be seen from Table 1 and FIGS. 8, 9 and 10, the maximal rates of increase in heart rate during sub-maximal exercise were positively related to the amount of work per kilogram of body mass that could be performed during the subsequent time-trial (i.e. the amount of work done is a marker of time-trial performance with more work done per kilogram of body mass indicating better performance). This finding indicates that a more rapid increase in heart rate during the warm-up was associated with better performance during the cycling time-trial.

Table 2 provides data evidencing a lack of any relationship between the rate of increase in heart rate during 30 seconds of rest followed by 5 minutes of sub-maximal exercise at workloads of 100 Watts, 125 Watts, 150 Watts, 175 Watts, 200 Watts or a self selected workload, and the steady state heart rate achieved during the final minute of each workload.

TABLE 2

| Sub-maximal Workload | Coefficient of Determination ($r^2$) | p-value |
|---|---|---|
| Self selected | 0.05 | 0.61 |
| 100 Watts | 0.003 | 0.90 |
| 125 Watts | 0.02 | 0.75 |
| 150 Watts | 0.09 | 0.46 |
| 175 Watts | 0.35 | 0.13 |
| 200 Watts | 0.34 | 0.13 |

As can be seen from Table 2, the steady-state heart rates that were reached during the final minutes of sub-maximal warm-ups were not related to the maximal rate of increase in heart rate. In other words, the rate of increase in heart rate did not predict the steady-state heart rate that would be reached during the warm-up.

Table 3 provides data evidencing a lack of any relationship between the steady state heart rates achieved during the final minute of exercise at workloads of 100 Watts, 125 Watts, 150 Watts, 175 Watts, 200 Watts or a self selected workload, and the work done during a subsequent 5 minute maximal cycling time trial.

TABLE 3

| Sub-maximal Workload | Coefficient of Determination ($r^2$) | p-value |
|---|---|---|
| Self selected | 0.04 | 0.65 |
| 100 Watts | 0.08 | 0.50 |
| 125 Watts | 0.12 | 0.40 |
| 150 Watts | 0.13 | 0.38 |
| 175 Watts | 0.15 | 0.34 |
| 200 Watts | 0.15 | 0.34 |

As can be seen from Table 3, the steady-state heart rates that were reached during the final minute of the sub-maximal warm-ups were not related to the amount of work that was done during the subsequent cycling time-trial. In other words, the steady-state heart rate during the warm-up did not predict performance during the subsequent cycling time-trial.

Table 4 shows the rate of increase in heart rate for a single individual during sub-maximal exercise at a workload of 100 Watts and at a self-selected sub-maximal workload prior to, and after, undertaking 2 hours of treadmill running at approximately 75% of maximal heart rate. The individual also performed a 5 minute maximal cycle time trial prior to and after the 2 hours of treadmill running (immediately after the sub-maximal exercise) and the amount of work done during each of these two cycle time trials is provided.

TABLE 4

|  | Workload | |
|---|---|---|
|  | Prior to 2 hour treadmill run | After 2 hour treadmill run |
| Work done during 5 minute cycle time trial (kJ/kg body mass) | 1.48 | 1.35 |
| Maximal rate of increase in heart rate during exercise at 100 Watts (beats/min/sec) | 2.256 | 0.889 |
| Maximal rate of increase in heart rate during exercise at a self-selected workload (beats/min/sec) | 1.137 | 0.736 |

As can be seen from Table 4 the amount of work that was done during the 5 minute cycle time trial following the 2 hour treadmill run was less than was performed during the 5 minute cycle time trial preceding the 2 hour treadmill run, indicating that the treadmill run had induced fatigue from which the individual had not fully recovered. It can also be seen that the maximal rates of increase in heart rate during sub-maximal exercise at a workload of 100 Watts and at a self-selected workload were slower following the 2 hour treadmill run than they were prior to the treadmill run. This confirms that the rate of increase in heart rate during sub-maximal exercise is slowed when an individual is fatigued (i.e. not fully recovered) and can thus be used as a marker of recovery, and/or for predicting the ability of the individual to perform at, above, or below, their optimal capacity.

Figure 11:
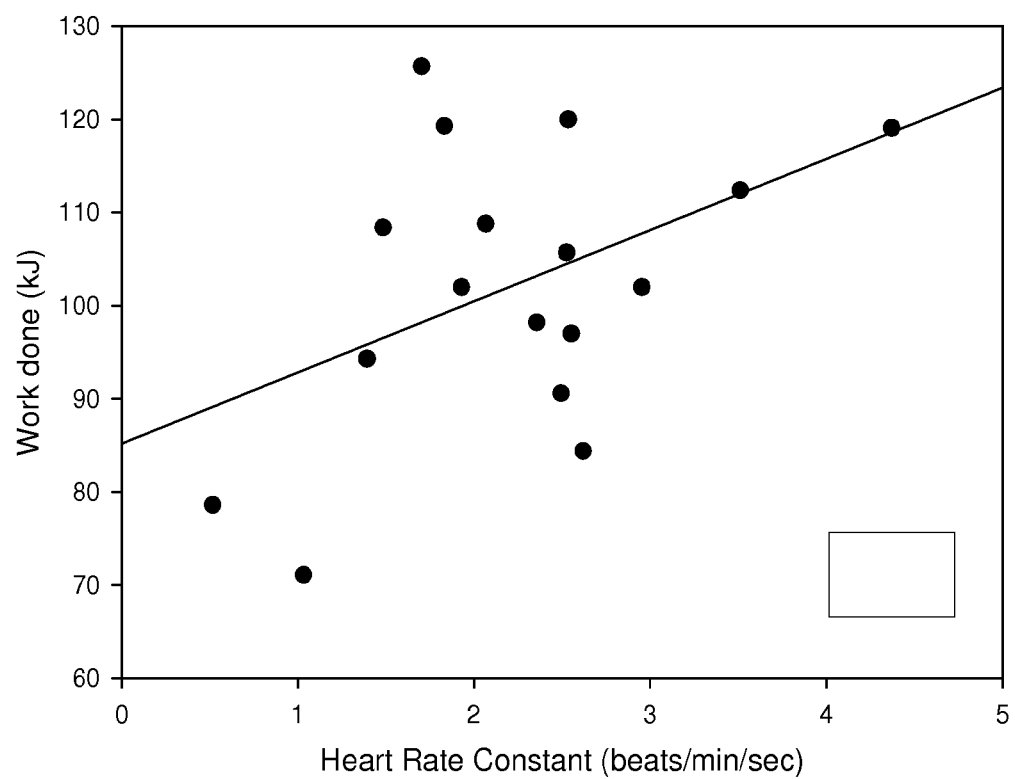
FIG. 11 is a graph showing the relationship between the rate of increase in heart rate in competitive male triathletes and cyclists during 30 seconds of rest followed by 5 minutes of sub-maximal exercise at a workload of 100 Watts, and the work done (in kilojoules) during a subsequent five minute maximal cycling time trial.
Figure 12:
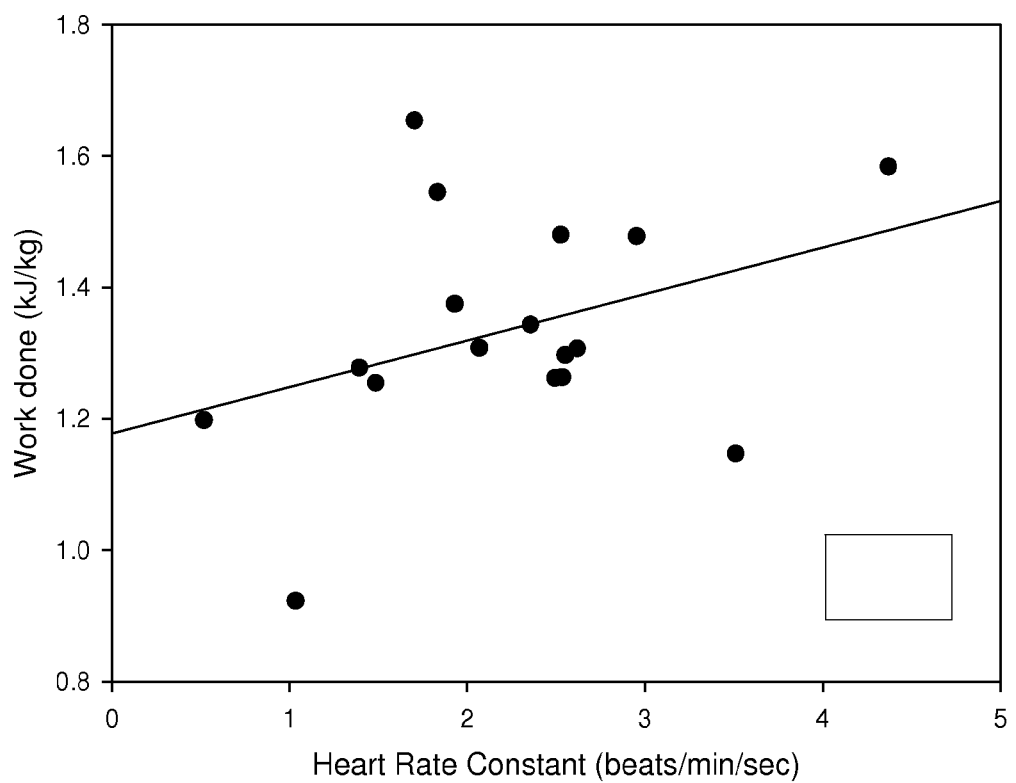
FIG. 12 is a graph showing the relationship between the rate of increase in heart rate in competitive male triathletes and cyclists during 30 seconds of rest followed by 5 minutes of sub-maximal exercise at a workload of 100 Watts, and the work done (in kilojoules per kilogram of body weight) during a subsequent five minute maximal cycling time trial.

Subsequently, 14 triathletes and 3 cyclists completed 5 minutes of cycling at a workload of 100 Watts while heart rate was recorded and the rate of increase in heart rate determined. They then performed a 5 minute cycle time trial. There was a positive relationship between the rate of increase in heart rate during the exercise at 100 Watts and the amount of work done during the 5 minute cycle time trial when expressed both as work done in kilojoules ($r^2$=0.21, P=0.06; FIG. 11) and kilojoules per kg of body weight ($r^2$=0.14, P=0.15; FIG. 12). This indicates that the rate of heart rate increase can be used to predict exercise performance for activities which rely on cardiorespiratory fitness. Given that low cardiorespiratory fitness is a risk factor for the development of cardiovascular disease, and performance during a 5 minute cycle time trial can be a marker of cardiorespiratory fitness, this also indicates that the rate of heart rate increase might be useful as a marker of cardiovascular disease risk.

There was also an inverse relationship between the rate of increase in heart rate during the exercise at 100 Watts and age (r=−0.40, P=0.11), indicating that the rate of heart rate increase was also related to a second risk factor for cardiovascular disease.

Figure 13:
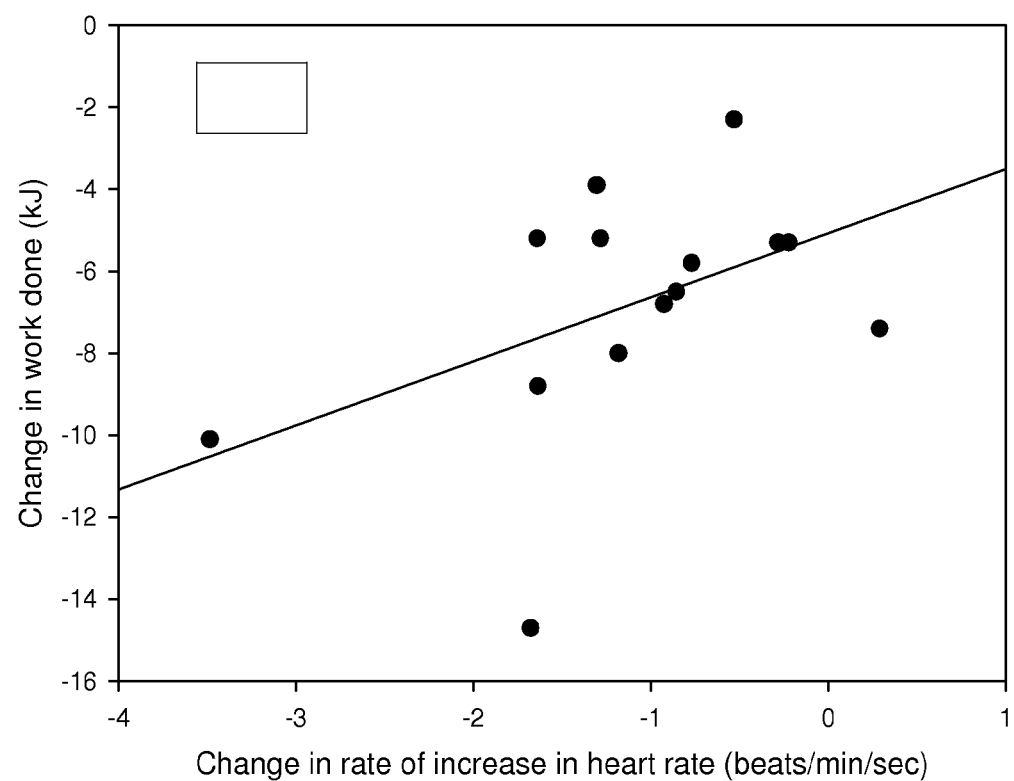
FIG. 13 is a graph showing the relationship between changes in the rate of increase in heart rate in competitive male triathletes during 30 seconds of rest followed by 5 minutes of sub-maximal exercise at a workload of 100 Watts, and changes in the work done (in kilojoules) during a subsequent five minute maximal cycling time trial prior to and after running for 2 hours on a treadmill to induce acute fatigue.

The 14 triathletes then ran for 2 hours on a treadmill at an exercise intensity that elicited 75-85% of their maximal heart rate. They then rested for 1 hour before repeating the 5 minutes of cycling at 100 Watts and the 5 minute cycle time trial. Due to the fatiguing effects of the 2 hours of running on the treadmill the triathletes performances in the 5 minute cycle time trial were reduced post-treadmill run, with the athletes performing significantly less work than they performed during the 5 minute cycle time trial completed prior to the treadmill run (prior to treadmill run 101±4 kilojoules versus post treadmill run 94±4 kilojoules; P<0.001). The rate of increase in heart rate during the 5 minutes of cycling at 100 Watts was also decreased after the treadmill run compared with the values achieved prior to the treadmill run (prior to treadmill run 2.25±0.26 beats/min/sec versus post treadmill run 1.14±0.18 beats/min/sec; P<0.001). Pre-exercise heart rates remained elevated (18±3 beats/min) above pre-treadmill run values at the commencement of the 5 minutes of cycling at 100 Watts after the treadmill run because heart rate had not completely recovered from the treadmill run. There was a tendency for the difference in the rate of heart rate increase in response to the 100 Watt workload between the pre- and post-treadmill run conditions to be inversely related to the magnitude of difference in pre-exercise heart rate, such that participants in whom the post-exercise heart rate was more elevated above pre-exercise values exhibited a greater reduction in the rate of increase in heart rate post-treadmill running ($r^2$=0.21, P=0.10). When this difference in pre-exercise heart rates was controlled for statistically (as a covariate) the change in time trial performance was found to be positively correlated with the change in the rate of heart rate increase (r=0.56, P<0.05; FIG. 13) such that a greater reduction in performance during the 5 minute cycle time trial was associated with a greater reduction in the rate of heart rate increase during the preceding 5 minutes of cycling at 100 Watts.

In a subsequent study 3 competitive male cyclists undertook two weeks of light training and two weeks of heavy training, with the order of training randomised. On the final day of each two week training period they performed 5 minutes of exercise at a power output of 100 Watts and the rate of increase in heart rate was determined as previously described. This was followed by a 5 minute cycle time trial and the work done during the time trial was recorded.

The purpose of this protocol was to evaluate the effects of 2 weeks of fatigue-inducing hard training on performance during the 5 minute cycle time trial and whether any change in performance was associated with a change in the rate of heart rate increase assessed during the preceding 5 minutes of cycling at a workload of 100 Watts.

One of the cyclists was unable to train on the day preceding testing following the hard training program and therefore had a day to recover before undergoing the test protocol. This person improved their performance in terms of the amount of work done (i.e. in kilojoules) in the 5 minute time trial compared with their time-trial performance after the two weeks of light training, presumably because the training had been sufficient to induce a performance improvement when sufficient time was allowed for the athlete to recover from the acute fatiguing effects of the training program. The other two cyclists did not perform as well after the two weeks of heavy training compared with the two weeks of light training (i.e. did less work [in kilojoules] during the 5 minute time trial) due to the fatigue induced by the heavy training and there being insufficient time between the final training session and the testing session to allow them to fully recover.

In the cyclist that performed better in the 5 minute cycle time trial after the two weeks of heavy training the rate of heart rate increase during the preceding 5 minutes of exercising at a workload of 100 Watts was faster, and in the two cyclists that performed worse in the 5 minute cycle time trial the rate of increase in heart rate was slower (see Table 5).

TABLE 5

|  | Light training | | Heavy training | | Difference (heavy minus light) | |
|---|---|---|---|---|---|---|
| ID | HRI (beats/min/sec) | Work (kJ) | HRI (beats/min/sec) | Work (kJ) | HRI (beats/min/sec) | Work (kJ) |
| 1 | 1.484 | 108.4 | 1.894 | 112.7 | 0.410 | 4.3 |
| 2 | 2.776 | 120 | 2.745 | 119.7 | −0.031 | −0.3 |
| 3 | 2.365 | 98.2 | 2.213 | 97 | −0.152 | −1.2 |

ID—participant identification number.
HRI—rate of heart rate increase during 5 minutes of cycle exercise at a work load of 100 Watts.
Work—work done (in kilojoules) during a 5 minute cycle time trial.

Figure 14:
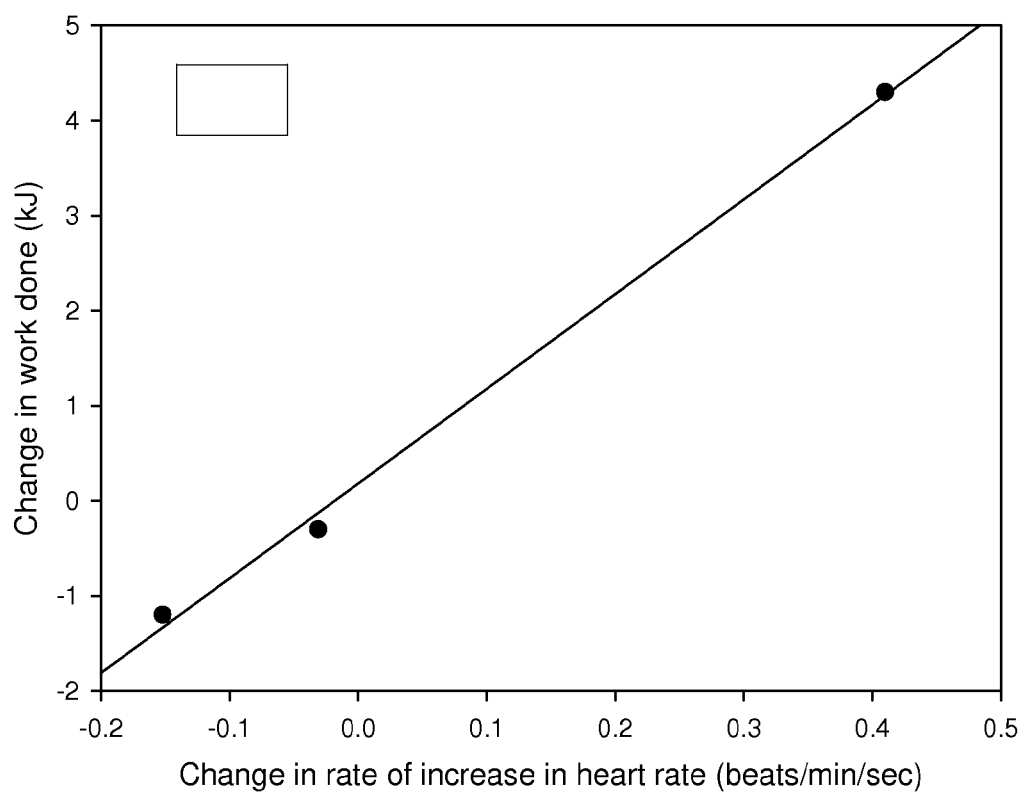
FIG. 14 is a graph showing the relationship between differences in the rate of increase in heart rate in competitive male cyclists during 30 seconds of rest followed by 5 minutes of sub-maximal exercise at a workload of 100 Watts, and differences in the work done (in kilojoules) during a subsequent five minute maximal cycling time trial after two weeks of light exercise training and two weeks of heavy exercise training.

Regression analysis indicated that the change in 5 minute cycle time trial performance (i.e. work done in kilojoules) was strongly associated with the change in the rate of increase in heart rate during the preceding 5 minutes of cycling at a workload of 100 Watts ($r^2>0.99$, P=0.03; FIG. 14). The average difference in pre-exercise heart rates preceding the 5 minutes of cycling at a power output of 100 Watts between the light and heavy training protocols was less than 1 beat/min, so no adjustment for differences in pre-exercise heart rate was performed (i.e. no statistical control for differences in pre-exercise heart rates was performed).

The differences in exercise performance (i.e. work done in kilojoules) during the 5 minute cycle time trial following the light training and heavy training protocols were only small, ranging from −1.2% to +3.8% and yet the change in the rate of increase in heart rate at a work load of 100 Watts was sensitive enough to detect these changes, with the magnitude of change in the rate of increase in heart rate being strongly related to even these small changes in exercise performance. This indicates that the assessment of the rate of increase in heart rate during submaximal exercise can be used to monitor even small changes in exercise performance that result either from training-induced improvements in fitness or training-induced decrements due to fatigue. The magnitude of the changes in performance were quite small yet this method is sensitive enough to track these small changes and should therefore be useful for monitoring small changes in the physiological readiness to perform exercise and thus predict changes in exercise performance in both novice and elite athletes, and members of the general public.

The rate of increase in heart rate at the onset of exercise reflects a balance between the rate of increase in sympathetic activation and parasympathetic withdrawal. A more rapid increase in heart rate at the onset of exercise suggests that there is either a greater rate of increase in sympathetic activity or more rapid withdrawal of parasympathetic activity. It seems most likely that it is the rate of change in the balance between sympathetic and parasympathetic nervous system activity that is important in terms of predicting the recovery state of an individual or predicting the ability of an individual to perform at, above, or below, their optimal capacity. On the other hand it is most likely the total levels of sympathetic and parasympathetic activity that ultimately determine the actual steady-state heart rate that is achieved during the sub-maximal exercise, with a higher level of sympathetic activity and lower parasympathetic activity resulting in a higher steady-state heart rate, and a lower level of sympathetic activity and a higher level of parasympathetic activity resulting in a lower heart rate. This would be consistent with our understanding that fitter people have lower sympathetic and higher parasympathetic tone and have lower heart rates during exercise at a given exercise intensity. However, the data described here found no relationship between the rate of increase in heart rate and the actual heart rate that was achieved during steady-state sub-maximal exercise, nor was there any relationship found between the steady-state heart rate during sub-maximal exercise and the work done during the subsequent 5 minute cycling time trial. This indicates that the rate of increase in heart rate most likely reflects the rate of change in the balance between sympathetic and parasympathetic nervous system activity rather than the balance of the total amounts of activity. Given that at the onset of exercise the withdrawal of parasympathetic activity precedes the increase in sympathetic activity, the more rapid increase in heart rate seen in our experiments most likely reflects a greater level of parasympathetic regulation, which is then withdrawn rapidly at the onset of exercise. However, regardless of the underlying mechanism, a more rapid increase in heart rate at the onset of exercise would be likely to more quickly meet the blood flow requirements to support exercise and thus reduce any impact of insufficient matching of blood flow to the demand for blood flow, and thus reduce any potential negative impact on athletic performance. Indeed a more rapid increase in heart rate during sub-maximal exercise was shown to be associated with a higher level of performance during a subsequent 5-minute cycle time-trial.

The advantage of being able to assess readiness to perform during an exercise test (which is reflective of the physiological readiness to perform and/or the recovery status of an individual) by simply assessing heart rate during sub-maximal exercise provides a simple non-invasive method that could easily be used during a warm-up to inform a coach or athlete regarding their recovery state or their expected or predicted ability to perform.

The relationship between the maximal rate of increase in heart rate during sub-maximal exercise and subsequent performance during the 5-minute cycling time trial was strongest (i.e. highest $r^2$ value) at workloads of 100 Watts and 200 Watts, suggesting that performance of exercise at these workloads will provide the most sensitive prediction of the physiological readiness to perform exercise, and could be used by individuals who have access to ergometers which allow for controlling the exercise workload. Testing was subsequently undertaken in triathletes and cyclists at a workload of 100 Watts and it was demonstrated that changes in the rate of increase in heart rate at this workload were able to track small changes in subsequent exercise performance during a 5 minute cycle time-trial.

The relationship between the maximal rate of increase in heart rate during sub-maximal exercise and subsequent performance during the 5-minute cycling time trial was also statistically significant when a self-selected sub-maximal workload was undertaken (i.e. $r^2=0.69$, P=0.01) indicating that this method of predicting physiological readiness to perform exercise can also be used by individuals who do not have access to ergometers, but can instead just exercise at an intensity that they freely choose without having to be able to determine the actual workload.

EXAMPLE 2

Cardiovascular Disease Risk Study

In order to establish that the rate of increase in heart rate when exercising at a standardised work load of 100 Watts can be used as an early marker of future cardiovascular disease risk the rate of heart rate increase is determined in a large sample of healthy adults who are free of cardiovascular disease. The participants are then be followed over a period of up to 10 years and data on morbidity and mortality from cardiovascular disease is collected by accessing government health databases.

This data set is then used to determine associations between the rate of heart rate increase at baseline and the risk of morbidity and mortality from cardiovascular disease. Based on the findings of the present invention, it would be anticipated that a lower rate of heart rate increase when exercising at a work load of 100 Watts at baseline would be predictive of a greater risk of future cardiovascular morbidity and mortality compared with a faster rate of heart rate increase.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. A method for determining a recovery state of an individual from an athletic activity, the method including:
   (a) subjecting the individual to a sub-maximal physical activity;
   (b) measuring the heart rate of the individual during the sub-maximal physical activity;
   (c) determining the maximal rate of increase in heart rate of the individual during the sub-maximal physical activity;
   (d) comparing the determined maximal rate of increase in heart rate of the individual with a predetermined reference measurement; and
   (e) determining the recovery state of the individual from the athletic activity on the basis of the comparison.

2. The method according to claim 1, wherein:
   (i) the slower the maximal rate of increase in heart rate of the individual during the sub-maximal physical activity compared to the predetermined reference measurement, the lower the recovery state of the individual from the athletic activity;
   (ii) if the maximal rate of increase in heart rate of the individual during the sub-maximal physical activity is the same as the predetermined reference measurement, the individual has recovered from the athletic activity; or
   (iii) if the maximal rate of increase in heart rate of the individual during the sub-maximal physical activity is faster than the predetermined reference measurement, the individual has recovered from the athletic activity and has improved fitness.

3. The method according to claim 1, wherein the heart rate of the individual is measured during the 30 seconds preceding the sub-maximal physical activity and during the first five minutes of the sub-maximal physical activity.

4. The method according to claim 1, wherein the sub-maximal physical activity is a warm-up activity of a pre-scribed or non-prescribed workload.

5. The method according to claim 1, wherein a heart rate monitor is used to measure the heart rate of the individual during the sub-maximal physical activity.

6. A method for predicting an individual's ability to perform an athletic activity at, above, or below, their optimal capacity, the method including:
   (a) subjecting the individual to a sub-maximal physical activity prior to the athletic activity;
   (b) measuring the heart rate of the individual during the sub-maximal physical activity;
   (c) determining the maximal rate of increase in heart rate of the individual during the sub-maximal physical activity;
   (d) comparing the determined maximal rate of increase in heart rate of the individual with a predetermined reference measurement; and
   (e) predicting the individual's ability to perform the athletic activity at, above, or below, their optimal capacity on the basis of the comparison.

7. The method according to claim 6, wherein:
   (i) a maximal rate of increase in heart rate of the individual during the sub-maximal physical activity that is slower than the predetermined reference measurement indicates that the individual will perform the athletic activity below their optimal capacity;
   (ii) a maximal rate of increase in heart rate of the individual during the sub-maximal physical activity that is faster than the predetermined reference measurement indicates that the individual will perform the athletic activity above their optimal capacity; or (iii) a maximal rate of increase in heart rate of the individual during the sub-maximal physical activity that is the same as the predetermined reference measurement indicates that the individual will perform the athletic activity at their optimal capacity.

8. The method according to claim 6, wherein the heart rate of the individual is measured during the 30 seconds preceding the sub-maximal physical activity and during the first five minutes of sub-maximal physical activity.

9. The method according to claim 6, wherein the sub-maximal physical activity is a warm-up activity of a pre-scribed or non-prescribed workload.

10. The method according to claim 6, wherein a heart rate monitor is used to measure heart rate of the individual during the sub-maximal physical activity.

11. A device for determining a recovery state of an individual from an athletic activity, the device including:
    (a) a heart rate measurement unit for measuring the heart rate of the individual during a sub-maximal physical activity;
    (b) a maximal rate of increase in heart rate determination unit for determining the rate of increase in heart rate of the individual during the sub-maximal physical activity;
    (c) a comparison unit for performing a comparison between the determined maximal rate of increase in heart rate of the individual and a predetermined reference measurement; and
    (d) a recovery state determination unit for determining the recovery state of the individual from the athletic activity on the basis of the comparison.

12. The device according to claim 11, wherein:
    (i) the slower the maximal rate of increase in heart rate of the individual during the sub-maximal physical activity compared to the predetermined reference measurement, the lower the recovery state of the individual;
    (ii) if the maximal rate of increase in heart rate of the individual during the sub-maximal physical activity is the same as the predetermined reference measurement, the individual has recovered from the athletic activity; or
    (iii) if the maximal rate of increase in heart rate of the individual during the sub-maximal physical activity is faster than the predetermined reference measurement, the individual has recovered from the athletic activity and has improved fitness.

13. A device for predicting an individual's ability to perform an athletic activity at, above, or below, their optimal capacity, the device including:
    (a) a heart rate measurement unit for measuring the heart rate of the individual during a sub-maximal physical activity;
    (b) a maximal rate of increase in heart rate determination unit for determining the maximal rate of increase in heart rate of the individual during the sub-maximal physical activity;
    (c) a comparison unit for performing a comparison between the determined maximal rate of increase in heart rate of the individual and a predetermined reference measurement; and
    (d) a prediction determination unit for predicting the individual's ability to perform the athletic activity at, above, or below, their optimal capacity on the basis of the comparison.

14. The device according to claim 13, wherein:
(i) a maximal rate of increase in heart rate of the individual during the sub-maximal physical activity that is slower than the predetermined reference measurement indicates that the individual will perform the athletic activity below their optimal capacity;
(ii) a maximal rate of increase in heart rate of the individual during the sub-maximal physical activity that is faster than the predetermined reference measurement indicates that the individual will perform the athletic activity above their optimal capacity; or (iii) a maximal rate of increase in heart rate of the individual during the sub-maximal physical activity that is the same as the predetermined reference measurement indicates that the individual will perform the athletic activity at their optimal capacity.

15. A computer software product, including coded instructions for executing a computer process in a digital processor, wherein the computer process determines a recovery state of an individual from an athletic activity, or predicts an individual's ability to perform an athletic activity at, above, or below, their optimal capacity, and wherein the computer process includes:
(a) inputting a heart rate measurement obtained from the individual during a sub-maximal physical activity conducted prior to the athletic activity;
(b) determining the maximal rate of increase in heart rate of the individual during the sub-maximal physical activity;
(c) performing a comparison between the determined maximal rate of increase in heart rate of the individual and a predetermined reference measurement; and
(d) determining the recovery state of the individual on the basis of the comparison, or predicting the individual's ability to perform the athletic activity at, above, or below, their optimal capacity on the basis of the comparison.

16. A method for determining a marker of a recovery state of an individual from an athletic activity or for predicting an individual's ability to perform an athletic activity at, above, or below, their optimal capacity, wherein the marker is the rate of increase in heart rate of the individual during a sub-maximal physical activity.

17. The method for determining the marker according to claim 16, wherein:
(i) a slower the maximal rate of increase in heart rate of the individual during the sub-maximal physical activity that is slower than a predetermined reference measurement indicates a lower recovery state of the individual from the athletic activity, or indicates that the individual will perform the athletic activity below their optimal capacity;
(ii) a maximal rate of increase in heart rate of the individual during the sub-maximal physical activity that is the same as the predetermined reference measurement indicates that the individual has recovered from the athletic activity, or indicates the individual will perform the athletic activity at their optimal capacity; or (iii) a maximal rate of increase in heart rate of the individual during the sub-maximal physical activity that is faster than the predetermined reference measurement indicates that the individual has recovered from the athletic activity and has improved fitness, or indicates that the individual will perform the athletic activity above their optimal capacitly.

18. The method for determining the marker according to claim 16, wherein the maximal rate of increase in heart rate of the individual is determined from heart rate measurements obtained from the individual, wherein the heart rate measurements are obtained during the 30 seconds preceding the sub-maximal physical activity and during the first five minutes of the sub-maximal physical activity.

19. The method for determining the marker according to claim 16, wherein the sub-maximal physical activity is a warm-up activity of a prescribed or non-prescribed workload.

20. The method for determining the marker according to claim 16, wherein a heart rate monitor is used to obtain heart rate measurements of the individual during the sub-maximal physical activity.

* * * * *